United States Patent
Herken et al.

(10) Patent No.: US 10,842,711 B2
(45) Date of Patent: *Nov. 24, 2020

(54) SYSTEM AND METHOD FOR DISTINGUISHING MANUAL FROM AUTOMATED CPR

(71) Applicant: ZOLL Medical Corporation, Chelmsford, MA (US)

(72) Inventors: Ulrich R Herken, Medford, MA (US); Gary A Freeman, Waltham, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 475 days.

This patent is subject to a terminal disclaimer.

(21) Appl. No.: 15/892,719

(22) Filed: Feb. 9, 2018

(65) Prior Publication Data
US 2018/0161240 A1   Jun. 14, 2018

Related U.S. Application Data

(63) Continuation of application No. 15/349,143, filed on Nov. 11, 2016, now Pat. No. 9,968,514, which is a
(Continued)

(51) Int. Cl.
*A61N 1/39*        (2006.01)
*A61N 1/08*        (2006.01)
(Continued)

(52) U.S. Cl.
CPC ......... *A61H 31/006* (2013.01); *A61B 5/0402* (2013.01); *A61B 5/046* (2013.01);
(Continued)

(58) Field of Classification Search
CPC .......... A61H 31/005; A61H 2201/5007; A61H 2230/04; A61N 1/39; A61N 1/3925; A61N 1/3987; A61N 1/3993
See application file for complete search history.

(56) References Cited

U.S. PATENT DOCUMENTS

| 4,770,164 A | 9/1988 | Lach et al. |
| 6,066,106 A | 5/2000 | Sherman et al. |

(Continued)

OTHER PUBLICATIONS

Gruben, et al., Sternal Force-Displacement Relationship During Cardiopulmonary Resuscitation, 115 Journal of Biomechanical Engineering 195 (May 1993).

*Primary Examiner* — Allen Porter
(74) *Attorney, Agent, or Firm* — Zoll Medical Corporation

(57) ABSTRACT

A system for use during administration of cardiopulmonary resuscitation (CPR) chest compressions on a victim is described. The system includes a chest compression monitor that includes a motion sensor configured to generate signals indicative of the victim's chest motion and a control system communicatively coupled to the chest compression monitor and configured to receive the generated signals, detect compression waveform features representative of the chest compressions based on the received signals, compare the features to a pre-determined criterion that distinguishes between a manual source of the chest compressions and a piston-based chest compression device source, determine whether the source of the chest compressions is the manual or the piston-based chest compression device source based on the comparison, and generate an output based on whether the source of the chest compressions is determined to be the manual or the piston-based chest compression device source.

25 Claims, 14 Drawing Sheets

Related U.S. Application Data continuation of application No. 14/605,700, filed on Jan. 26, 2015, now Pat. No. 9,522,285, which is a continuation of application No. 14/015,494, filed on Aug. 30, 2013, now Pat. No. 8,942,803.

(51) Int. Cl.

| | | |
|---|---|---|
| *A61H 31/00* | (2006.01) | |
| *A61B 5/046* | (2006.01) | |
| *A61B 5/00* | (2006.01) | |
| *A61B 5/0402* | (2006.01) | |

(52) U.S. Cl.
CPC ......... *A61B 5/4836* (2013.01); *A61H 31/005* (2013.01); *A61H 31/007* (2013.01); *A61N 1/3925* (2013.01); *A61N 1/3987* (2013.01); *A61H 2201/0176* (2013.01); *A61H 2201/10* (2013.01); *A61H 2201/1207* (2013.01); *A61H 2201/1619* (2013.01); *A61H 2201/1645* (2013.01); *A61H 2201/1654* (2013.01); *A61H 2201/1664* (2013.01); *A61H 2201/5007* (2013.01); *A61H 2201/5025* (2013.01); *A61H 2201/5043* (2013.01); *A61H 2201/5048* (2013.01); *A61H 2201/5058* (2013.01); *A61H 2201/5064* (2013.01); *A61H 2201/5079* (2013.01); *A61H 2201/5084* (2013.01); *A61H 2201/5097* (2013.01); *A61H 2230/045* (2013.01)

(56) References Cited

U.S. PATENT DOCUMENTS

| | | | |
|---|---|---|---|
| 6,213,960 | B1 | 4/2001 | Sherman et al. |
| 6,553,257 | B2 | 4/2003 | Snyder et al. |
| 6,865,413 | B2 | 3/2005 | Halperin et al. |
| 7,056,295 | B2 | 6/2006 | Halperin |
| 7,220,235 | B2 | 5/2007 | Geheb et al. |
| 7,226,427 | B2 | 6/2007 | Steen |
| 7,308,304 | B2 | 12/2007 | Hampton et al. |
| 7,410,470 | B2 | 8/2008 | Escudero et al. |
| 7,569,021 | B2 | 8/2009 | Sebelius et al. |
| 7,650,181 | B2 | 1/2010 | Freeman et al. |
| 7,734,344 | B2 | 6/2010 | Ideker et al. |
| 7,837,636 | B2 | 11/2010 | Tjolsen et al. |
| 7,996,081 | B2 | 8/2011 | Bystrom et al. |
| 8,062,239 | B2 | 11/2011 | Sherman et al. |
| 8,121,681 | B2 | 2/2012 | Hampton et al. |
| 8,224,442 | B2 | 7/2012 | Bystrom et al. |
| 8,433,405 | B2 | 4/2013 | Bystrom et al. |
| 8,433,407 | B2 | 4/2013 | Chapman et al. |
| 8,465,292 | B2 | 6/2013 | Nysaether et al. |
| 8,478,401 | B2 | 7/2013 | Freeman |
| 8,560,065 | B2 | 10/2013 | Eerden |
| 8,657,764 | B2 | 2/2014 | King |
| 8,666,480 | B2 | 3/2014 | Halperin et al. |
| 8,690,804 | B2 | 4/2014 | Nilsson et al. |
| 8,725,253 | B2 | 5/2014 | Johnson et al. |
| 8,774,945 | B2 | 7/2014 | Freeman |
| 8,868,179 | B2 | 10/2014 | Quan et al. |
| 9,149,411 | B2 | 10/2015 | Coleman et al. |
| 9,173,807 | B2 | 11/2015 | Freeman |
| 9,445,697 | B2 | 9/2016 | Wu |
| 9,486,390 | B2 | 11/2016 | Centen et al. |
| 9,844,487 | B2 | 12/2017 | Nilsson et al. |
| 2005/0101889 | A1 | 5/2005 | Freeman et al. |
| 2009/0204161 | A1 | 8/2009 | Powers et al. |
| 2009/0260637 | A1 | 10/2009 | Sebelius et al. |
| 2010/0198117 | A1 | 8/2010 | Itnati |
| 2011/0040217 | A1 | 2/2011 | Centen |
| 2011/0166490 | A1 | 7/2011 | Woerlee et al. |
| 2011/0301513 | A1 | 12/2011 | Freeman |
| 2013/0023781 | A1 | 1/2013 | Freeman et al. |
| 2013/0060172 | A1 | 3/2013 | Palazzolo et al. |
| 2013/0085425 | A1 | 4/2013 | Monsieurs et al. |

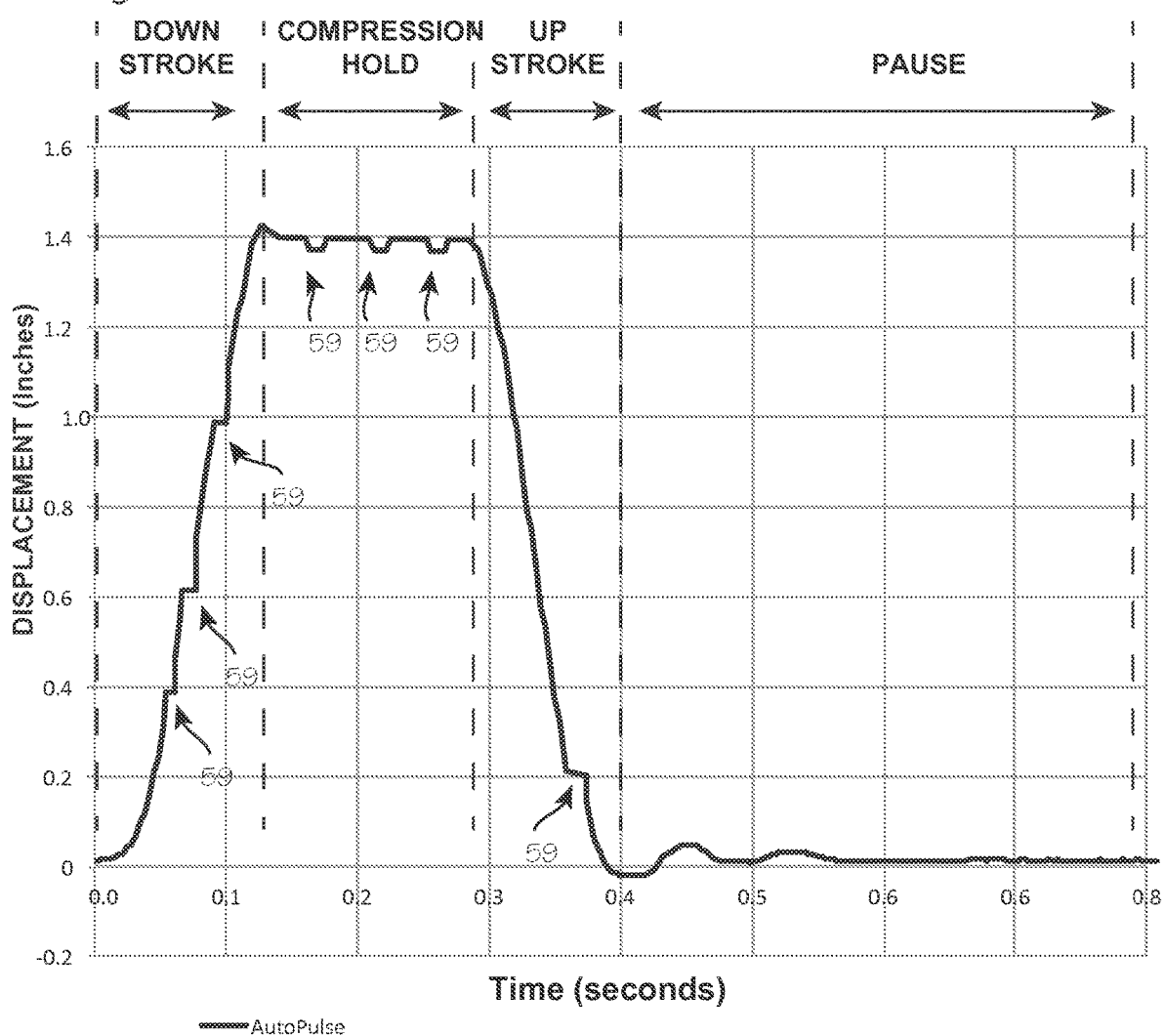

SYSTEM AND METHOD FOR DISTINGUISHING MANUAL FROM AUTOMATED CPR

CROSS-REFERENCE TO RELATED APPLICATIONS

This application is a continuation under 35 U.S.C. § 120 of U.S. patent application Ser. No. 15/349,143 filed Nov. 11, 2016 which is a continuation of U.S. patent application Ser. No. 14/605,700 filed Jan. 26, 2015 and issued as U.S. Pat. No. 9,522,285 which is a continuation of U.S. application Ser. No. 14/015,494 filed Aug. 30, 2013 and issued as U.S. Pat. No. 8,942,803. All subject matter set forth in each of the above referenced applications is hereby incorporated by reference in their entirety into the present application as if fully set forth herein.

FIELD OF THE INVENTIONS

The inventions described below relate to the field of CPR and defibrillation.

BACKGROUND OF THE INVENTIONS

For cardiac arrest victims, resuscitation includes CPR chest compressions, rescue breathing, and defibrillation. Defibrillation is performed only when a reliable ECG can be obtained from the victim, and CPR chest compressions induce so much noise in the ECG signal that they must typically be halted for a quiet period of 12 to 15 seconds in order for an AED to obtain enough uncorrupted ECG data to make a reliable decision to shock a patient. During this quiet period, any blood flow induced by CPR compression ceases, and this is highly undesirable.

Also, as described in various references, including our prior patent, Sherman, et al. Chest Compression device with Electro-Stimulation, U.S. Pat. No. 6,213,960 (Apr. 10, 2001) it is beneficial to apply cardioverting shock from the defibrillator during specific periods in the CPR compression cycle, typically near the most compressed state of the chest, but best after the end of the compression or downstroke and as the chest is expanding in the upstroke. Though beneficial, synchronization of cardioverting shock with CPR chest compressions must be performed with two obstacles in mind. Firstly, it is best to avoid interruption of compressions, as is historically needed to obtain clean ECG data. Second, synchronized shock should not be performed if the CPR compression are provided manually by a CPR provider because it risks shocking the person (which can cause cardiac arrest in the CPR provider).

The first problem is solved by the motion artifact reduction techniques described in Halperin, ECG Signal Processor and Method, U.S. Pat. No. 6,865,413 (Mar. 8, 2005). Halperin, and the See Thru CPR® technology embodied in various defibrillators, enable the analysis of the ECG signals while CPR chest compressions are ongoing. The second problem is addressed by providing CPR chest compressions with an automated chest compression device, such as ZOLL Circulations AutoPulse® chest compression device. ZOLL's automated external defibrillators (AED's) can be interconnected with the AutoPulse® device, and are programmed to apply defibrillating/cardioverting shock during a point in the compression cycle in which the heart is highly compressed and responsive to shock (this is provided in an operating mode that must be selected by the operator of the AED).

It would be beneficial to provide an AED which can analyze ECG data during CPR chest compressions without interconnection with a chest compression device, but is nonetheless operable to provide electrotherapy such as defibrillating and/or cardioverting shock while compressions are ongoing, and also provide electrotherapy synchronized to the compression cycle when CPR chest compressions are performed by an automated systems, but inoperable to provide synchronized defibrillating/cardioverting shock when CPR chest compressions are performed manually (by a person that may be in electrical communication with the CPR victim) while compressions are ongoing.

SUMMARY

The devices and methods described below provide for improved administration of defibrillation during CPR. Using a chest compression monitor, which is now used to measure chest compression depth during the course of CPR, a signal corresponding to chest wall motion (acceleration, velocity, or depth signals) is generated and is used to determine an optimal point within the compression cycle for shock. A control system, such as an AED control box that receives and interprets ECG signals from electrodes on the victim's chest, and controls a defibrillator to deliver defibrillating/cardioverting shock through the electrodes, also receives and interprets the signals corresponding to the chest wall motion. As described below, this system can also be used determine whether CPR is being provided by a chest compression device or by a CPR provider.

To ensure that a defibrillator does not shock a patient while a CPR provider is performing manual compressions (which would result in shocking the CPR provider, and possibly inducing cardiac arrest in the rescuer), the compression waveform obtained from the chest compression monitor can be analyzed to detect CPR chest compressions and determine if the patient is being compressed manually or by machine, and the AED can automatically determine to shock, or not to shock, while CPR chest compressions are ongoing, based on the source of compressions, to ensure that a CPR provider is not shocked while compressing a patient. For shocks delivered by machine, the AED can synchronize the delivery of shock with the compression stroke, without the need to connect the AED to the compression device or rely on feedback from the compression device. Also, because the compression waveform of belt-based and piston-based chest compression devices are sufficiently distinct, the compression waveform obtained from the chest compression monitor can be analyzed to determine if the patient is being compressed by a compression belt or by a piston, and the AED can automatically determine to shock, or not to shock, based on the source of compressions, to ensure that shock is not provided during compressions provided by a system for which synchronized shock has not been validated.

The system can be used to control the delivery of any electrotherapy while CPR chest compressions are ongoing. Electrotherapy may include defibrillating shock, cardioverting shock, electrical nerve stimulation, and pulsed magnetic fields used for cardiac stimulation.

BRIEF DESCRIPTION OF THE DRAWINGS

FIG. 15 illustrates a compression waveform which is varied through operation of a chest compression device so as to be uniquely identifiable.

DETAILED DESCRIPTION OF THE INVENTIONS

Figure 1:
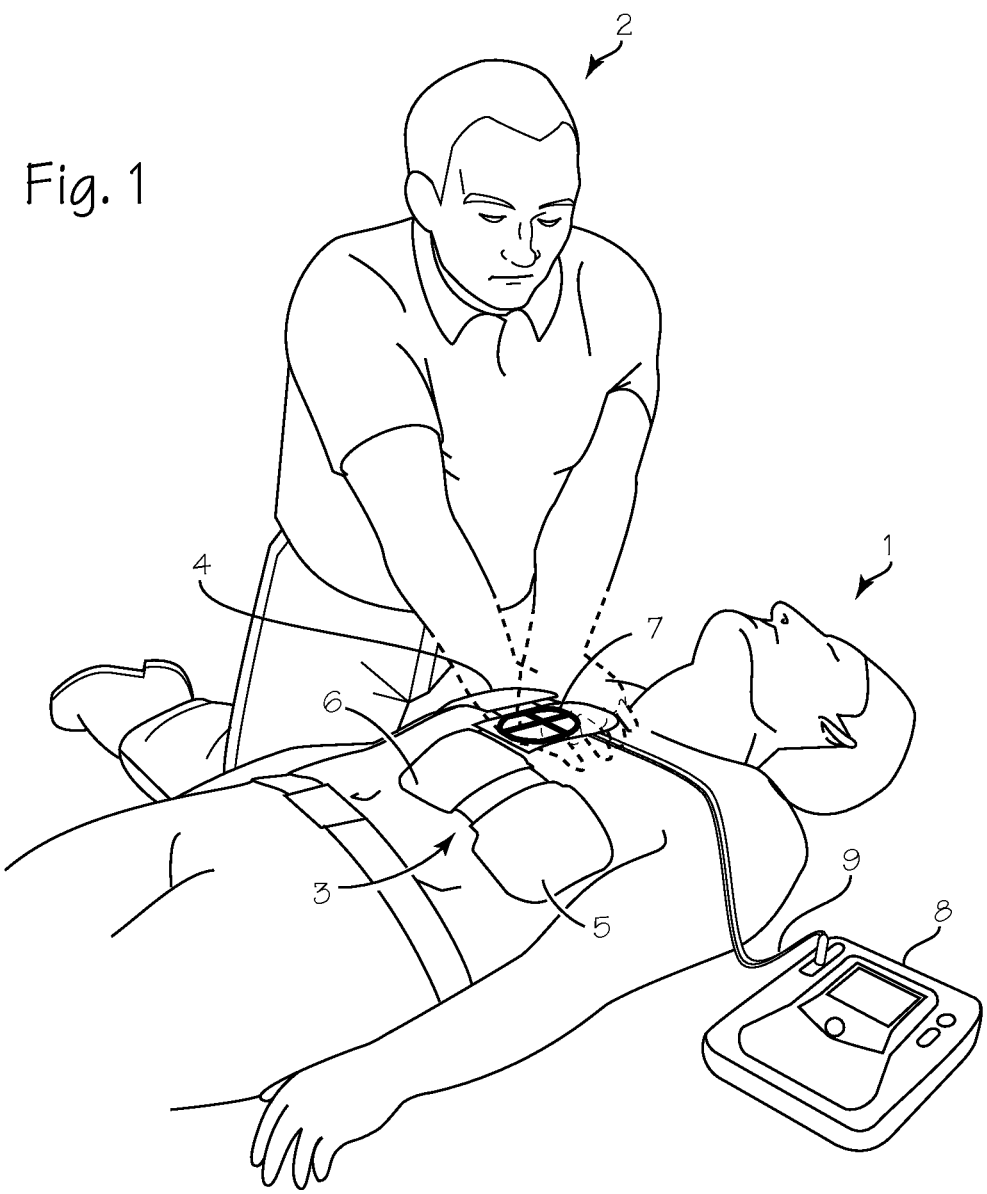
FIG. 1 illustrates the use of a chest compression monitor in use on a patient, with a rescuer providing manual chest compressions.

FIG. 1 illustrates the use of a chest compression monitor in use on a patient 1, with a rescuer 2 providing manual chest compressions. As part of the resuscitation effort, the rescuer has applied an ECG electrode assembly 3 on the patient's chest. This assembly includes a sternum electrode 4, an apex electrode 5, and sternal bridge 6. A chest compression monitor 7 is disposed within the sternal bridge, sandwiched between layers of foam that comprise the bridge. The bridge, along with the cross-hair indicia, serves as a template for proper placement of the chest compression monitor over the sternum of the victim which, and ensures that the sternal and apex electrodes are properly placed (for patients of a wide variety of sizes). The electrode assembly is connected to a defibrillator 8 (through cable 9) which is fitted with a control system or systems capable of controlling (and programmed to control) ECG and defibrillating functions and capable of controlling (and programmed to control) the chest compression monitor functions of interpreting sensor signals (acceleration signals, velocity signals, or distance signals, for example) from the chest compression monitor, determining the depth of compressions from those sensor signals, and generating and providing feedback to the rescuer. The feedback may be both audio feedback (voice prompts) provided through an annunciator or visual feedback provided on a display. These compression monitor functions can also be accomplished by a control system built into the chest compression monitor itself, as described in Halperin '413 and as implemented in our PocketCPR® device. The feedback can include prompts to compress more deeply, prompts to compress at a faster or slower rate, and prompts to quickly and completely release the chest of the patient after each compression.

Figure 2:
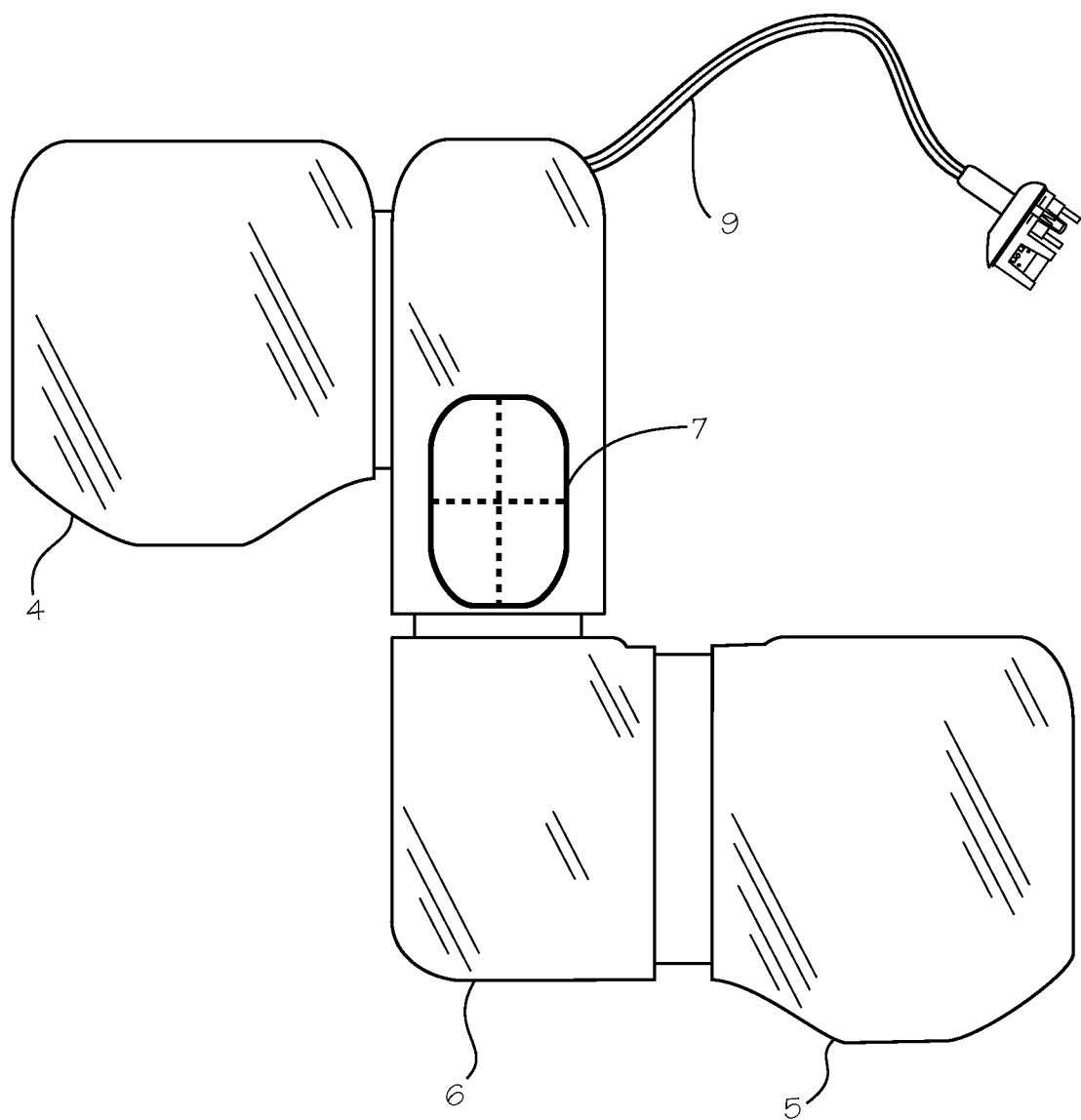
FIG. 2 is a top view of the electrode assembly FIG. 1.

FIG. 2 is a top view of the electrode assembly of FIG. 1, which includes the chest compression monitor 7. In this view, the location of the sternal electrode 4 and apex electrode 5, and the chest compression monitor 7 within the bridge 6 are more clearly shown. The chest compression monitor is disposed within a housing or on an equivalent structure, which itself is disposed within the electrode locating bridge 6 shown in FIG. 1, sandwiched between layers of foam, so that, when applied to the patient, the CPR chest compression monitor is disposed over the sternal notch of the patient. This chest compression monitor and its housing are referred to as a puck in the developing art.

Figure 3:
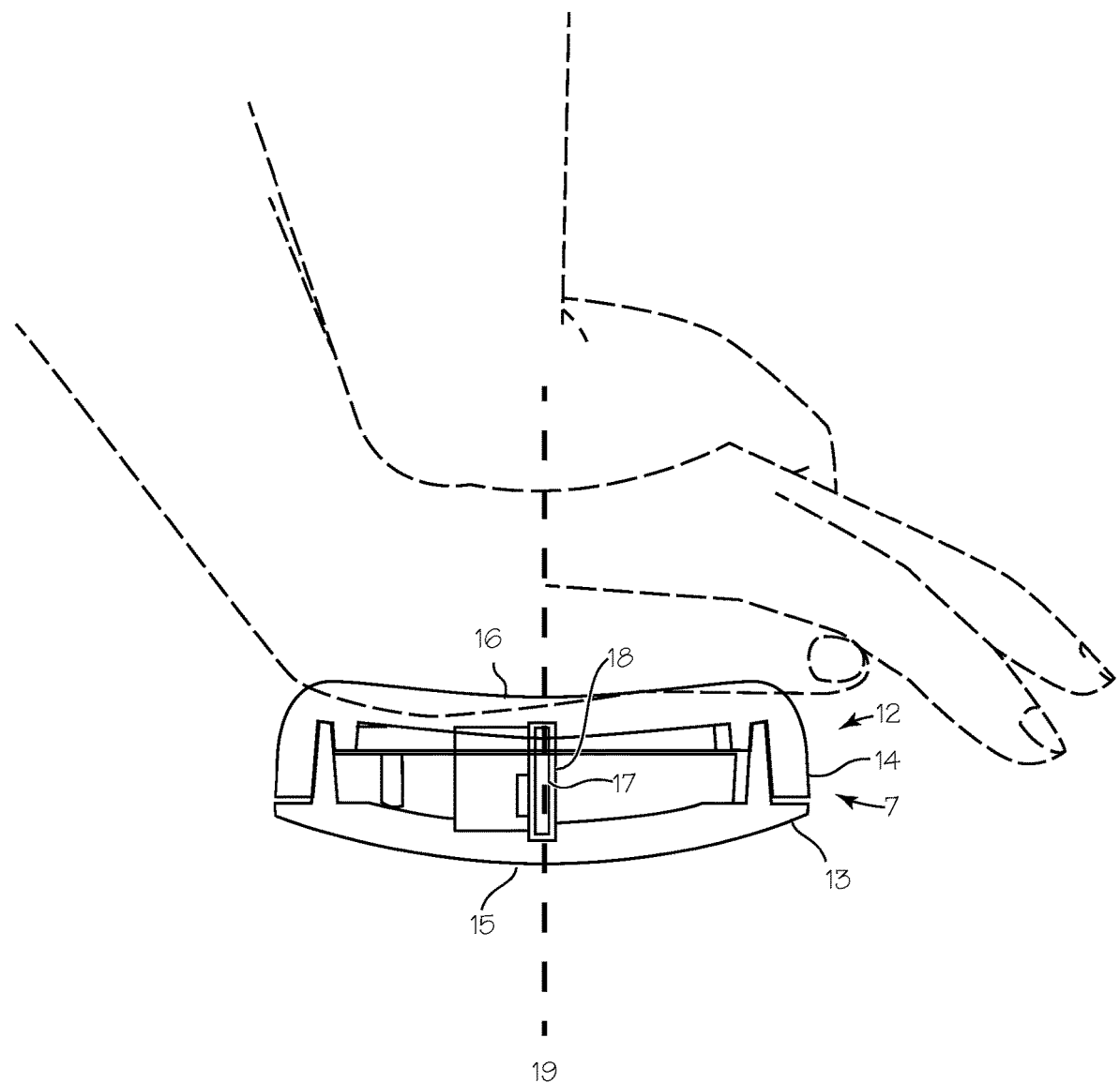
FIG. 3 illustrates the chest compression monitor as implemented in ZOLL Medical's Real CPR Help® chest compression monitor.

FIG. 3 illustrates the chest compression monitor 7 as implemented in ZOLL Medical's CPR Stat-padz® or CPR-D-padz®, and also in ZOLL Medical's Real CPR Help® chest compression monitor (a standalone device). The puck includes a housing 12 with a housing bottom portion 13 and housing top portion 14. The housing bottom portion has a slightly convex bottom surface 15 (which opposes the chest, or anterior surface of the patient's thorax), to conform to the patient's sternal notch. The housing top portion has a slightly concave top surface 16 (superficial, relative to the patient) which facilitates hand placement over the puck during use. The accelerometer assembly 17 that measures acceleration of the puck is disposed in its packaging and on a mounting board 18, within the housing. Typically, the accelerometer assembly is a multi-axis accelerometer assembly, with two or three distinct accelerometers arranged orthogonally to each other, capable of detecting acceleration on two or three orthogonal axes. Preferably, the axes are aligned in the chest compression monitor to coincide with the compression axis 19 (typically, the vertical axis which corresponds to the anterior/posterior axis of the patient when supine) and one or two axes orthogonal to the compression axis (typically two horizontal axes). With this arrangement, chest compression depth can be measured, as described in the Halperin patents. The accelerometer assembly may also comprise separate accelerometers, with two or three accelerometers rotatably mounted to the housing. As described in Halperin and Palazzolo, the accelerometers produce an acceleration signal corresponding to acceleration of the chest wall achieved during CPR chest compressions, and the control system processes this acceleration signal to determine compression depth. Also, as described in Geheb, the control system processes this acceleration signal to determine velocity, including the velocity of the chest wall during the period when the CPR provider should be releasing the chest to allow it to expand (the release velocity).

The chest compression monitor, as illustrated in FIGS. 1, 2 and 3, comprises a housing adapted to be held in fixed relation to the chest, specifically the anterior surface of the thorax over the sternum, so that during CPR chest compressions the movement of the chest compression monitor and sensors of the monitor closely correspond to downward and upward motion of the chest wall of the patient.

The accelerometer-based compression monitor is presented as the most convenient configuration for obtaining information regarding compression depth, velocity and acceleration. However, any device operable to sense compression depth, velocity and acceleration, or to sense signals or obtain data from which compression depth, velocity and acceleration may be derived or determined, may be used in place of the accelerometer based compression monitor. Thus, means for determining compression depth, velocity and acceleration can include the accelerometers described above, velocity sensors which directly measure velocity, and distance sensors or proximity sensors which track the displacement of the compression module. For example, the proximity sensors, including and ultrasonic distance sensor arrangement, optical distance sensors, magnetic motion sensors, RFID sensors and emitter/detector arrangements, for example those described in Freeman and Herken, Chest Compression Belt with Belt Position Monitoring System, U.S. Provisional App. 61/654,642 filed Jun. 1, 2012, incorporated herein by reference in its entirety, can be used to measure the actual displacement of the chest, and the control system can readily determine the velocity as the derivative of the displacement curve. A rheostat and mechanical linkage fixed to the puck may be used to measure the displacement, as described in Gruben et al., Sternal Force Displacement Relationship During Cardiopulmonary Resuscitation, 115 Journal of Biomedical Engineering 195 (May 1993) (which describes the use of mechanical linkages incorporating position sensing transducers to measure chest displacement during CPR), and from displacement data the control system can calculate the release velocity.

Geheb, et al., Method and Apparatus for Enhancement of Compressions During CPR, U.S. Pat. No. 7,720,235 (May 22, 2007) and Centen, et al., Reference Sensor for CPR Feedback Device, U.S. Pub. 2012/0083720 (Apr. 5, 2012) disclose a system for measuring chest compression depth using a magnetic field generator under the patient and an inductive coil, which senses movement through the magnetic field, as a velocity sensing system. This system can be used as a velocity sensor in the system described above, from which compression depth can be determined. Centen, Optical Techniques for The Measurement of Chest Compression Depth and Other Parameters During CPR, U.S. Pub. 2011/0040217 (Feb. 17, 2011) discloses a system for measuring chest compression depth using infrared optical illumination and detection of the reflected infrared light from the patient. This system can be used as a distance sensor in the system described above, from which velocity of the chest wall movement can be determined.

These and any other means for determining compression depth, velocity or acceleration may be used. Also, though a single sensor, and a single type of sensor, are sufficient to provide the necessary information to determine velocity and chest displacement, multiple sensors and sensor types can be used in any permutation. For example, a velocity sensor can be used to directly measure velocity, and a displacement sensor or measurement device (operable independently from the velocity sensor) can be used to directly measure displacement, such that the control system can determine velocity from the velocity sensor and determine displacement from the displacement sensor.

Figure 4:
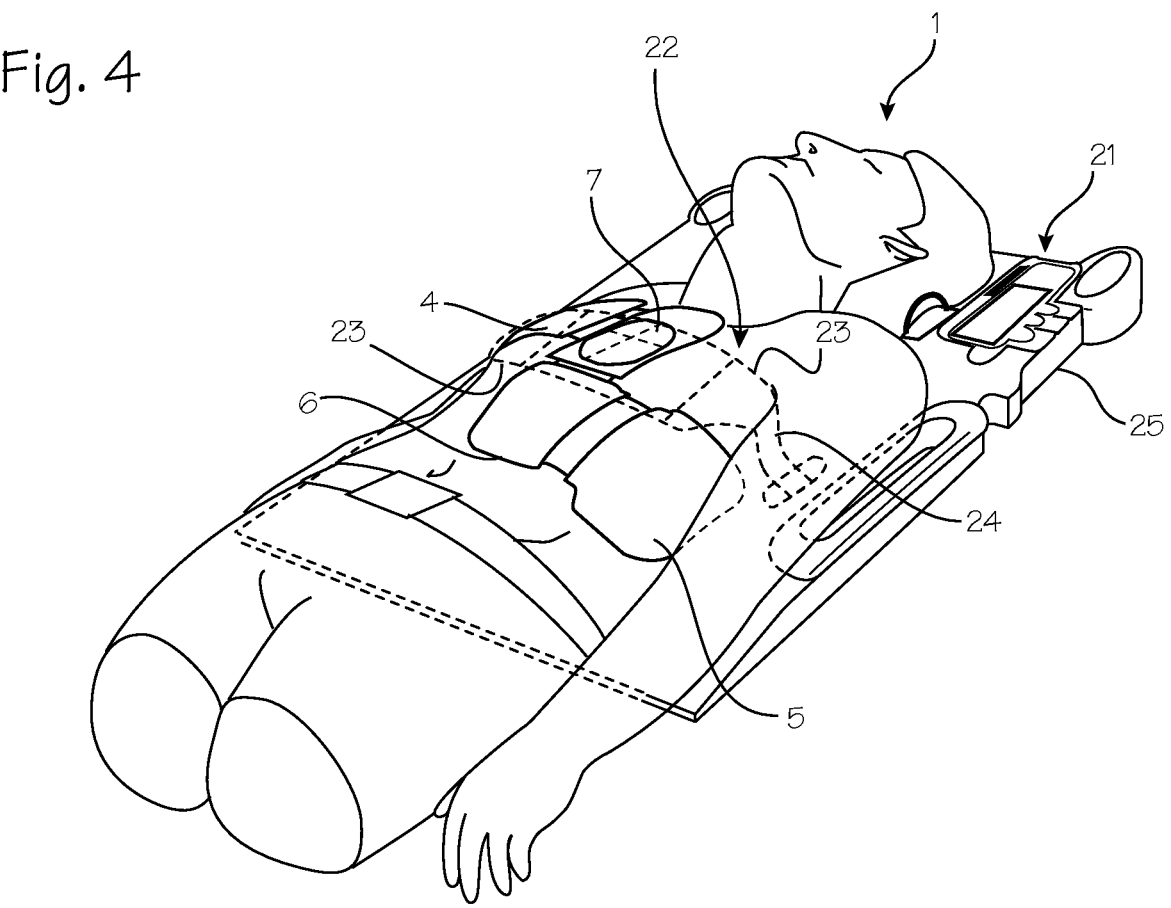
FIG. 4 illustrates the use of a chest compression monitor in use on a patient, with a chest compression device installed on the patient.

FIG. 4 illustrates the use of a chest compression monitor in use on a patient, with a chest compression device 21 installed on the patient 1. The chest compression device is described in our U.S. Pat. No. 7,410,470, and includes a compression belt 22 (shown in phantom) with load distributing panels 23 and pull straps 24 (one on each side of the patient) attached to a drive spool and a motor within the housing 25. As illustrated in this view, the ECG electrode assembly 3 is disposed on the patient's chest, under the load distributing band. This assembly includes the sternum electrode 4, the apex electrode 5, the sternal bridge 6 and the chest compression monitor 7 illustrated in FIG. 1. The chest compression monitor and electrodes are preferably connected to a defibrillator directly, but can be connected through a connection built into the housing. The chest compression monitor is disposed between the patient and the load distributing panels, above the sternum of the patient. The AutoPulse® compression device is capable of rapidly compression the patient's thorax and holding the thorax in a state of compression, during each compression cycle. The AutoPulse® compression device is also capable of holding the belt taught for a short period between each compression cycle. Compression achieved by the AutoPulse® compression device is readily identifiable by analysis of the compression waveform, as describe below.

Figure 5:
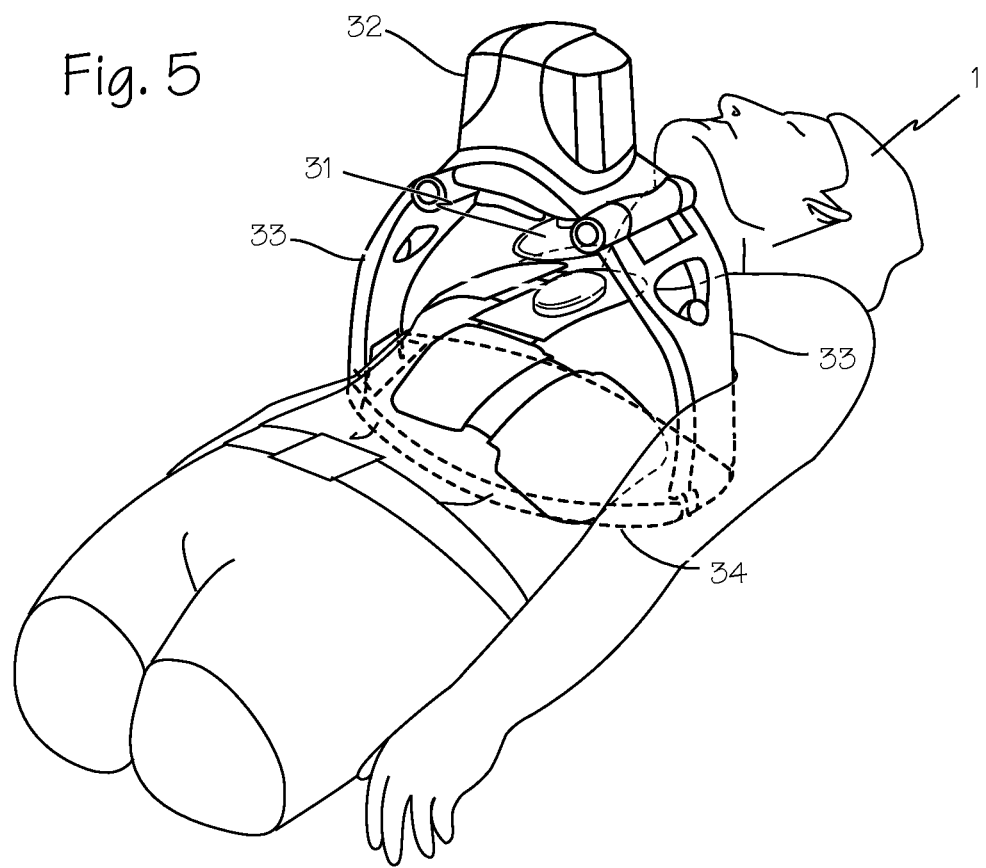
FIG. 5 illustrates the use of a chest compression monitor in use on a patient, with a piston-based chest compression device installed on the patient.

FIG. 5 illustrates use of a chest compression monitor in conjunction with a piston-based compression device. This device is described in Nilsson, et al., CPR Device and Method, U.S. Patent Publication 2010/0185127 (Jul. 22, 2010), Sebelius, et al., Support Structure, U.S. Patent Publication 2009/0260637 (Oct. 22, 2009), Sebelius, et al., Rigid Support Structure on Two Legs for CPR, U.S. Pat. No. 7,569,021 (Aug. 4, 2009), Steen, Systems and Procedures for Treating Cardiac Arrest, U.S. Pat. No. 7,226,427 (Jun. 5, 2007) and King, Gas-Driven Chest Compression Device, U.S. Patent Publication 2010/0004572 (Jan. 7, 2010), and operates on the same principle as the Thumper® chest compression device. The device uses a piston 30 and compression pad 31, driven by a motor disposed with motor housing 32 suspended over the patient's chest on support arms 33, and fixed in the anterior/posterior dimension relative to the patient with backboard 34. Piston-based compression devices are not currently capable of providing high or inter-compression holds during a compression cycle. Piston based compression is readily identifiable by analysis of the compression waveform, as describe below.

Figure 6:
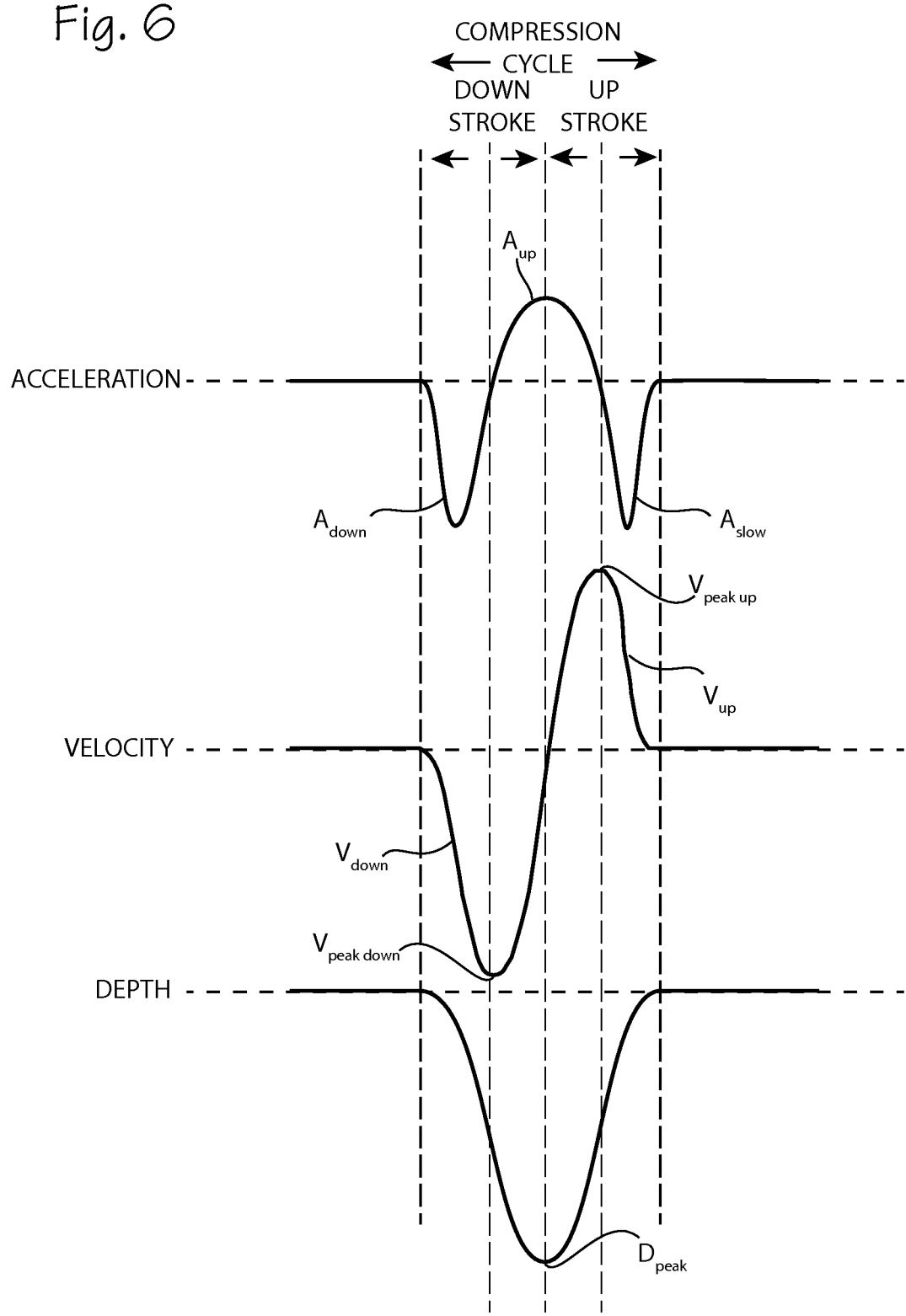
FIG. 6 illustrates the relationship of acceleration, velocity and compression depth for CPR chest compressions.

FIG. 6 illustrates the relationship of acceleration, velocity and compression depth (displacement) for CPR chest compressions. Any one of these values may be measured, and others may be determined, through straightforward integration or derivation, of the measured signal. FIG. 6 shows three compression waveforms: an acceleration waveform, a velocity waveform, and a compression depth waveform for an ideal compression cycle. A compression cycle includes a downstroke, an upstroke (a release portion), and perhaps some delay between a downstroke and a successive upstroke, or between an upstroke and a successive downstroke. Delay between a compression cycle and the succeeding compression cycle, in which the compression device remains taught or slightly compressed about or on the patient's chest is referred to as an inter-compression hold. (Delay with or without the inter-compression hold may be generically referred to as an inter-compression pause.) The compression cycle may also include compression hold, which is a delay between a downstroke and a successive upstroke (this is referred to as a high compression hold in our U.S. patent, Sherman, et al., Modular CPR Assist Device, U.S. Pat. No. 6,066,106 (May 23, 2000)).

As shown in FIG. 6, acceleration, chest wall velocity and chest wall depth correspond to each other during a compression cycle. When the CPR provider pushes or the chest compression device exerts compression force on the patient's chest, the chest and the compression module held in fixed relation to the chest are accelerated downwardly, experiencing a downward acceleration depicted as a negative acceleration $A_{down}$. Near the end of the downstroke, the acceleration $A_{down}$ slows to zero, and reverses to an upward acceleration $A_{up}$ as the CPR provider releases the compression and natural resilience of the thorax leads to expansion and upward rebound of the chest wall. This is reflected in the positive acceleration $A_{up}$ which quickly slows to zero as the chest reaches its fully expanded position. Upward movement decelerates at $A_{slow}$, and then returns to zero at the completion of the compression cycle. The cycles continue as the CPR provider repeatedly compresses the chest. The velocity curve follows the acceleration curve, with peak downward velocity $V_{peakdown}$ occurring when the downward acceleration $A_{down}$ falls to zero, and upward or release velocity $V_{up}$ increasing while the upward acceleration $A_{up}$ is positive, and $V_{peakup}$ occurring when $A_{up}$ falls to zero. The displacement of the chest reaches its deepest extent $D_{peak}$ when the downward velocity returns to zero, and returns to the original chest position during the period of upward velocity. As these curves are strictly related to each other, each curve can be determined from the others, and data regarding one parameter can be analyzed to determine the other parameters.

Figure 7:
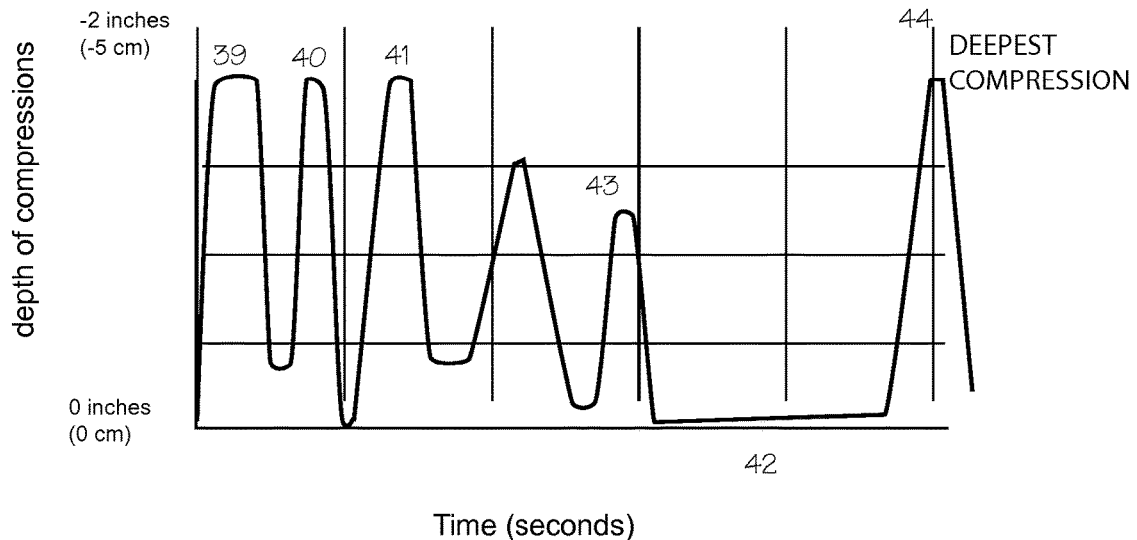
FIGS. 7, 8 and 9 illustrate compression waveforms representative of manual CPR, AutoPulse® CPR chest compressions, and piston CPR chest compressions.
Figure 8:
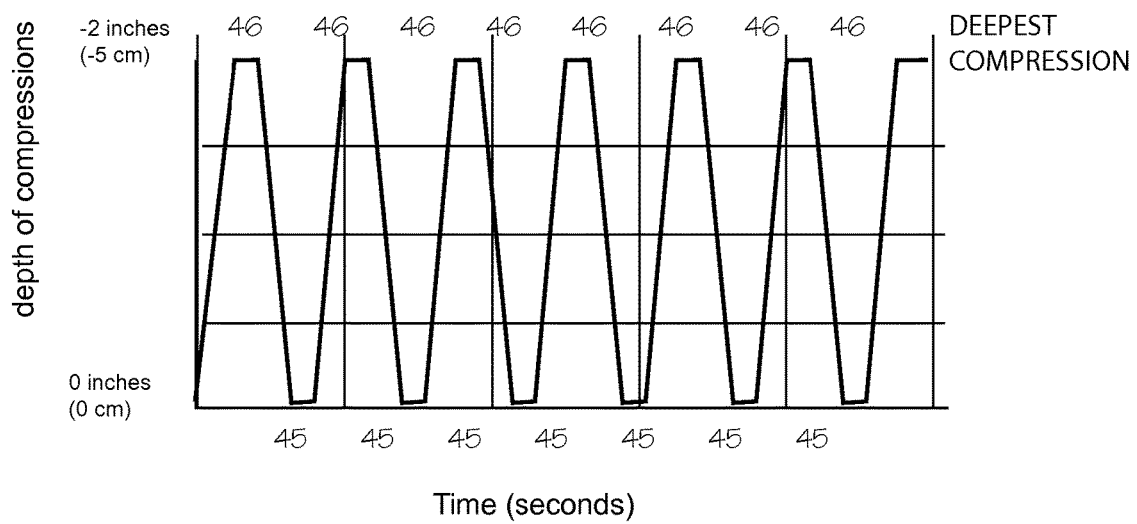
Figure 9:
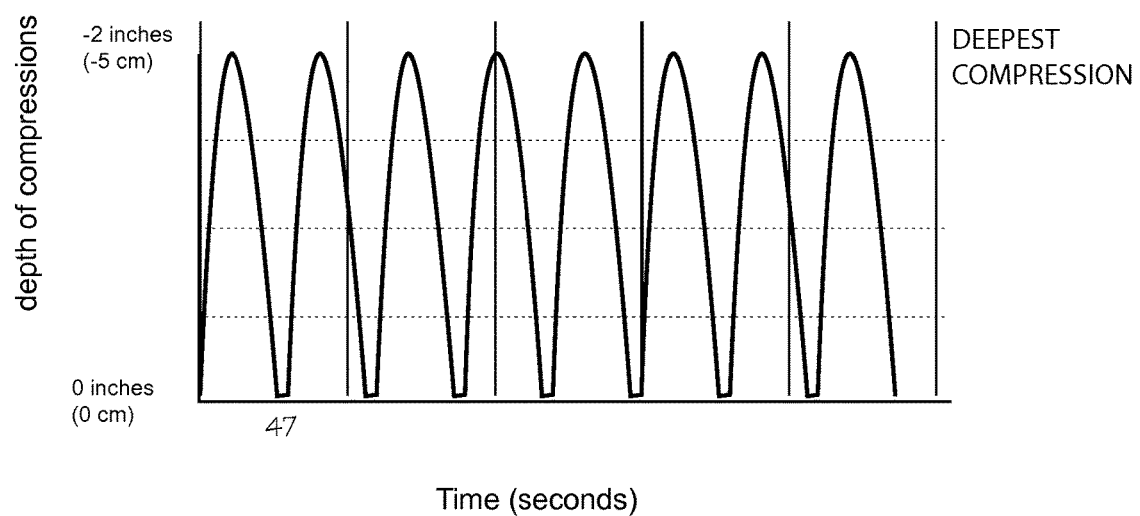

FIGS. 7, 8 and 9 illustrate compression waveforms representative of manual CPR, AutoPulse® belt CPR chest compressions, and LUCAS® piston-based CPR chest compressions. FIG. 7 illustrates a compression depth waveform that is typical for manual CPR. This waveform represents chest wall displacement as a function of time for a series of compressions. A seen in the graph, several characteristics, discernable through signal processing and feature extraction techniques, indicate that this waveform is characteristic of manual CPR:

the deepest portion of each compression is characterized by a very rounded appearance; there is little or no compression hold period in which the chest is held in a high state of compression;

the upstroke of each compression cycle follows immediately at the conclusion of the preceding downstroke;

the depth of compression varies significantly from one compression cycle to the next; and the periodicity of the compression cycles is variable.

As seen in the graph of FIG. 7, depth of compression during manual CPR is highly variable. Manual compressions, ideally would be a consistent 2.0 to 2.5 inches in depth (per ACLS Guidelines 2010). Consistency of depth is not critical, so long as the desired depth goal is met for most compressions. Inconsistency of depth of compression, though, is a discernable feature of the waveform that is indicative of manual CPR. Also, the rate of compression is variable, with some compressions closely spaced in time and some extended delays between compressions. When a CPR provider is attempting to compress continuously, the rate of compression varies, even though the CPR provider is attempting to compress at a consistent rate of 100 compressions per minutes. The periodicity (the interval between successive compressions) is irregular and highly variable. At perfect periodicity, a CPR provider would achieve one compression every 600 milliseconds, with precisely 600 milliseconds between each compression. Assuming perfect periodicity, each compression would be separated from the previous and subsequent compression by the same interval. The typical manual compression waveform deviates significantly from perfect periodicity. For example, one compression 39 maybe be followed by a subsequent compression 40 by about 600 milliseconds, while the next following compression 41 follows compression 40 by about 1000 milliseconds. Also, at point 42 there is a very long delay between compression 43 and 44, indicating the CPR provider has taken a short rest, and paused between compressions.

FIG. 8 illustrates an idealized compression waveform that is typical for automated CPR provided by the AutoPulse® chest compression device. (It is not an actual waveform, but a representation of the ideal waveform that the device would achieve under perfect conditions.) This waveform represents chest wall displacement as a function of time for a series of compressions. A seen in the graph, several characteristics, discernable through signal processing and feature extraction techniques, indicate that this waveform is characteristic of automated CPR provided by the AutoPulse®:

the deepest portion of each compression is characterized by a very flat appearance, indicating the compression hold achieved by the AutoPulse®;

the highest portion of each compression cycle is characterized by a very flat appearance, indicating the inter-compression hold achieved by the AutoPulse®;

the depth of compression is very consistent from one compression cycle to the next; and the periodicity of the compression cycles is very consistent, such that each compression is separated from the previous and subsequent compression by the same interval.

As seen in the graph of FIG. 8, the depth of compression achieved by the AutoPulse® chest compression device is very consistent. Compression depth may vary insubstantially, but for practical purposes, all compressions achieved by the device are the same depth. This perfect consistency is characteristic of chest compressions achieved by automated devices. Also, the rate of compression is very consistent, and essentially invariable, with each compression followed by the next succeeding compression at precise intervals (in this case, the AutoPulse® is programmed to accomplish compressions at a rate of 80 compressions per minute, so there should be 750 milliseconds between the initiation of each compression downstroke, and thus 750 milliseconds between each upstroke/release phase). The periodicity, as expected of machine compression, is very consistent. Each compression is separated from the previous and subsequent compression by the same interval. None of the variation seen in manual CPR is seen in this compression waveform. Also seen in this waveform are the holding periods characteristic of the AutoPulse®. These holding periods 45 and 46 appear at the top and bottom of each compression. These holding periods appear as short periods in which compression depth is not changing, or as flat spots in the compression waveform.

FIG. 9 illustrates an idealized compression waveform that is typical for automated CPR provided by the LUCAS® piston-based chest compression device. This waveform represents chest wall displacement as a function of time for a series of compressions. A seen in the graph, several characteristics, discernable through signal processing and feature extraction techniques, indicate that this waveform is characteristic of automated CPR provided by the LUCAS® piston-based chest compression device:

the deepest portion of each compression is characterized by a rounded appearance, indicating the absence of a compression hold achieved by the AutoPulse®;

the highest portion of each compression is characterized by a flat appearance, indicating the inter-compression hold achieved by the LUCAS® device;

the depth of compression is very consistent from one compression cycle to the next; and the periodicity of the compression cycles is very consistent.

This ideal waveform differs from the ideal AutoPulse® waveform in the in that there is no appreciable compression hold.

As seen in the graph of FIG. 9, the depth of compression achieved by the LUCAS® chest compression device is very consistent. Compression depth may vary insubstantially, but for practical purposes, all compressions achieved by the device are the same depth. This perfect consistency is characteristic of chest compressions achieved by automated devices. Also, the rate of compression is very consistent, and essentially variable, with each compression followed by the next succeeding compression at precise intervals (in this case, 600 milliseconds between the initiation of each compression downstroke, and thus 600 milliseconds between each upstroke/release phase). The periodicity, as expected of machine compression, is very consistent. Each compression is separated from the previous and subsequent compression by the same interval. None of the variation seen in manual CPR is seen in this compression waveform. Also seen in this waveform are the pauses characteristic of the Lucas®. These pauses 47 appear at the end of each upstroke, but there is no corresponding holding period at the bottom of each compression. This is because the Lucas® device does accomplish a compression hold or an inter-compression hold, but does pause momentarily between compressions. Thus the waveform provided by the Lucas® device is readily distinguishable from the waveform of the AutoPulse® device.

Figure 10:
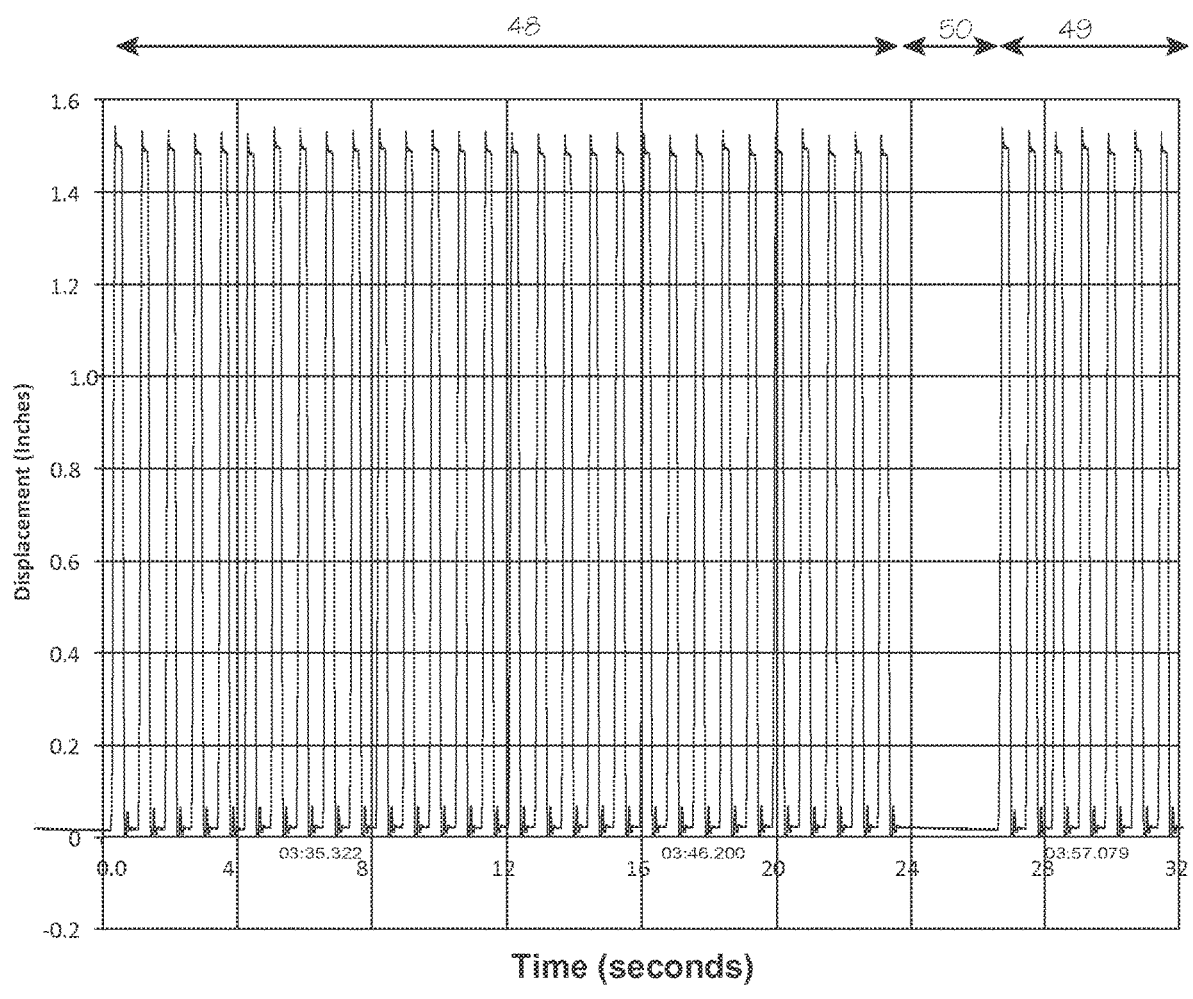
FIGS. 10 and 11 are actual waveforms from compression measured on a test manikin constructed to mimic the behavior of a typical median percentile male human under compression.
Figure 11:
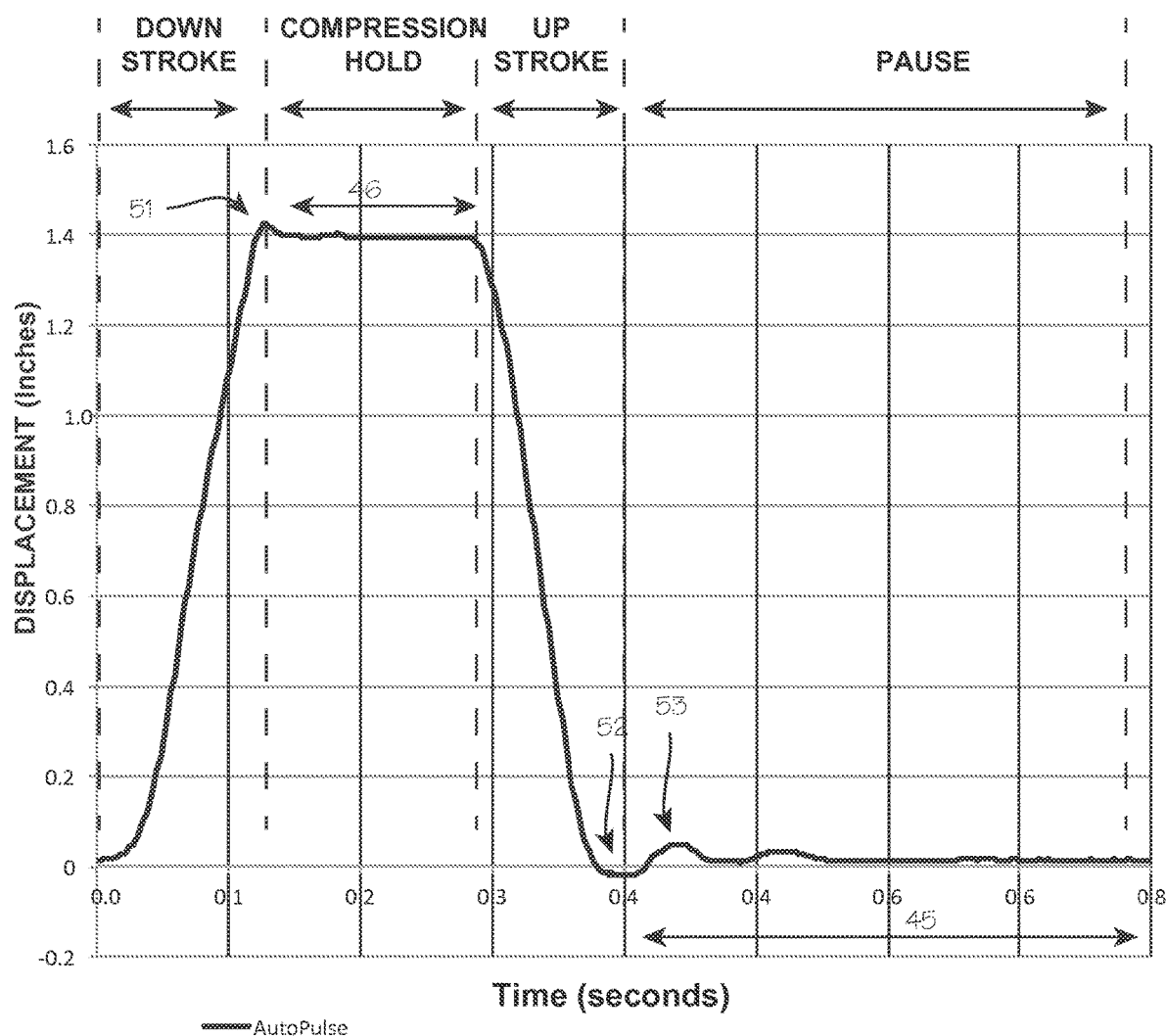

FIGS. 10 and 11 are actual waveforms from AutoPulse® compressions measured on a test manikin constructed to mimic the behavior of a typical median percentile male human under compression. FIG. 10 shows a series of compressions (item 48) separated by a subsequent series of compressions (item 49) by a ventilation pause (item 50). Compressions are accomplished at a rate of 80 compressions per minute, or 750 milliseconds per compression cycle. FIG. 11 shows a single compression cycle, including an inter-compression pause (for the AutoPulse®, the belt is held taut during this period between compressions), the compression downstroke (in which the belt is rapidly tightened to compress the chest), a compression hold (in which the belt holds the chest in a maximum state of compression), and an upstroke/release period (in which the compressive force on the chest is removed by releasing the belt). As appears from FIG. 10, the compressions are quite uniform in depth and periodicity. As appears from both FIGS. 10 and 11, actual compression waveforms include artifacts. One such artifact is the slight over-shoot at the transition between the compression downstroke and the high-compression hold, which appears as a peak 51 in each waveform. Another artifact appears as an upstroke overshoot peak 52 at the end of the upstroke, followed by a cinching overshoot peak 53 as the system cinches the belt to keep it taut between compressions, after which measured compression depth settles into a stable, inter-compression hold period 45. As in the idealized waveform of FIG. 8, readily visible characteristics of the waveform include the compression hold period 46, the inter-compression hold period 45, and the sharp transition between the hold periods and the compression downstroke and upstroke.

Figure 12:
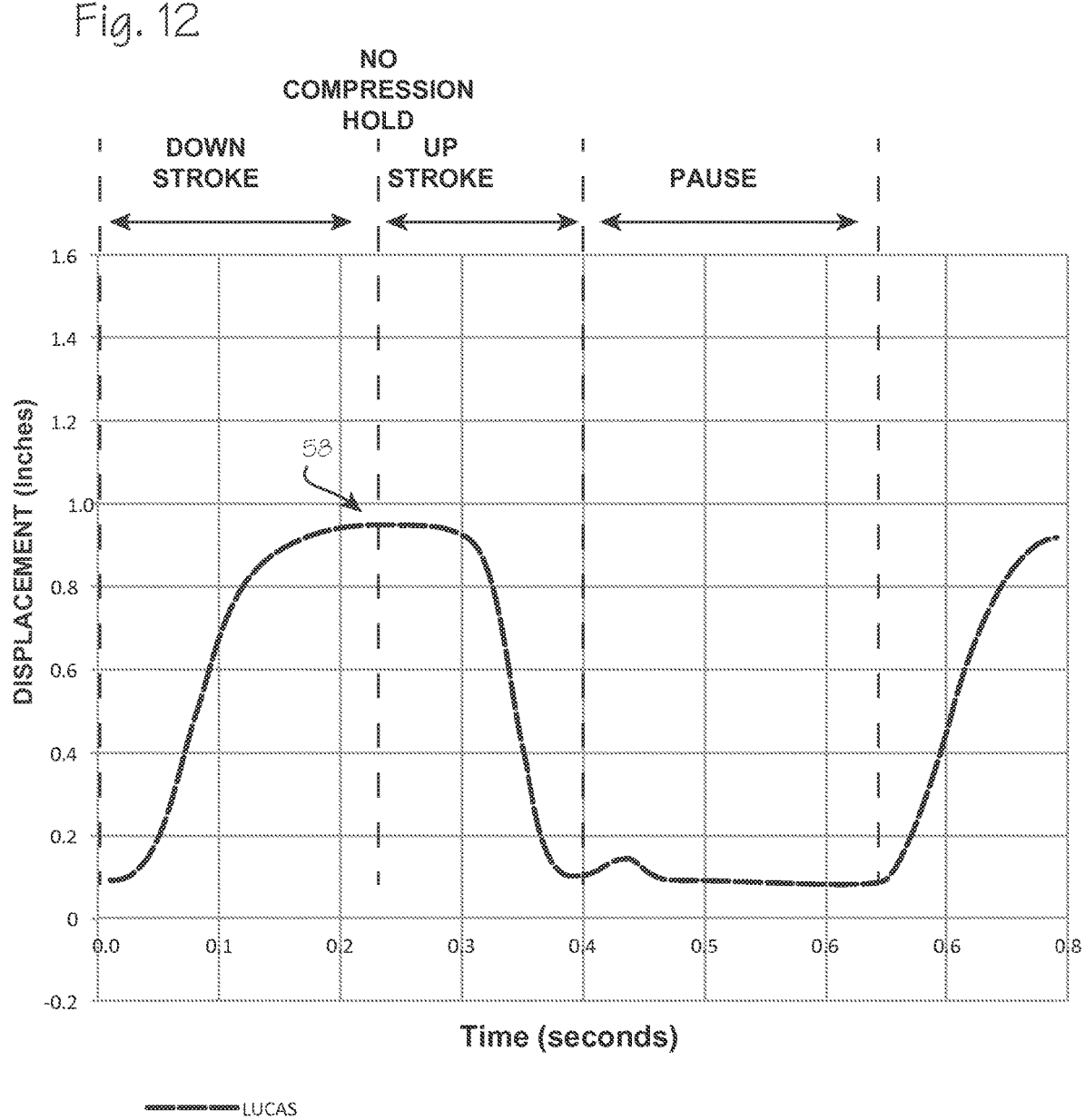
FIG. 12 is an actual waveform from Lucas® compression device also measured on a test manikin constructed to mimic the behavior of a typical median percentile male human under compression.

FIG. 12 is an actual waveform from Lucas® compression device also measured on a test manikin constructed to mimic the behavior of a typical median percentile male human under compression. This waveform does not include overshoot artifacts seen in the AutoPulse® waveforms of FIGS. 10 and 11. It is characterized by a rounded peak at the end of the compression stroke and immediate transition into the release period without an intervening compression hold, which occurs at a maximum point marked as item 58. Transition from the inter-compression pause to the compression stroke, transition from the compression stroke to the release period, and transition from the release period to the following inter-compression pause, are gradual and not sharply defined. Also, the compressions are accomplished at 100 compressions per minute, for a compression cycle of 600 milliseconds. As with the AutoPulse®, the compressions are quite uniform in depth and periodicity.

Figure 13:
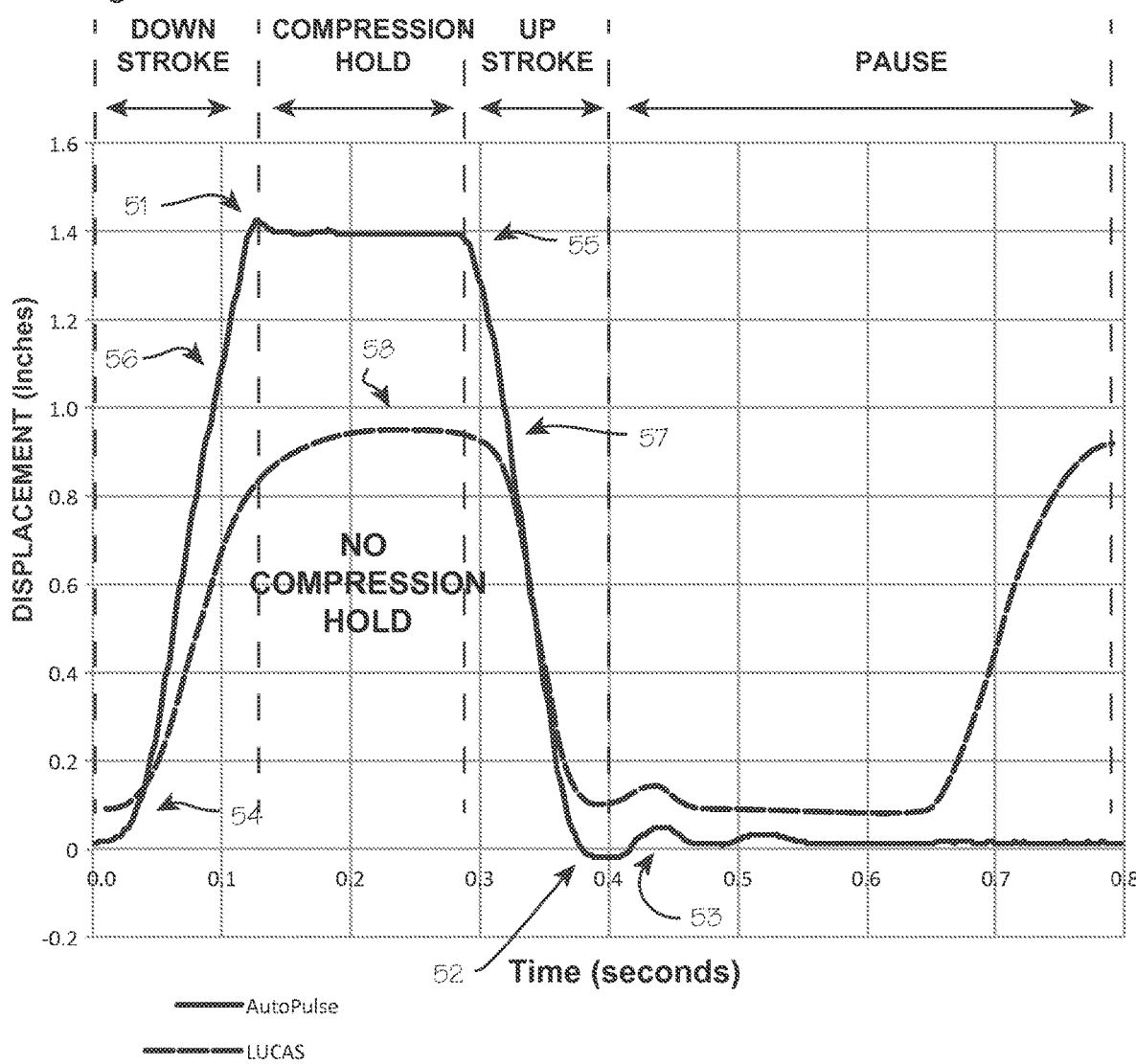
FIG. 13 illustrates the waveforms of FIGS. 11 and 12 superimposed on a single graph for comparison.

Additional differences between AutoPulse® compression waveforms and Lucas® compression waveforms appear from the overlay of compression waveforms on a single graph, as shown in FIG. 13. In FIG. 13, the waveforms of FIG. 11 and FIG. 12 are superimposed on each other. From this overlay, additional waveform characteristics which differ between the two waveform are apparent. For example, the peak velocity and acceleration of the AutoPulse® compression stroke are higher than the peak velocity and acceleration of the Lucas® waveform. Thus, a predetermined acceleration or velocity value at a predetermined point in the compression cycle can be used to distinguish belt-compression from piston compression, and distinguish automated chest compression from manual chest compression. For example, a chest wall velocity of 14 inches/second or more on the compression downstroke would be indicative of automated chest compression achieved by a belt compression device (this depends on known operating parameters of extant belt compression devices). The curvature of the transition (marked as item 54) into the downstroke is greater, indicating higher acceleration achieved by the AutoPulse® at the start of the downstroke. The curvature of the transition (marked as item 55) from the compression hold into the upstroke is greater, indicating higher acceleration achieved by the AutoPulse® at the start of the upstroke. Also, the slope of the waveform during the downstroke is steeper (marked as item 56), indicating higher velocity, and the slope of the waveform during the upstroke is steeper (marked as item 57), indicating higher velocity as compared to the curvature of the transition and the slope for the Lucas® device. The AutoPulse® waveform contains a very sharp transition from the compression hold to the change in depth during the release period and the release waveform is steeper, which again indicates that the peak upward acceleration and velocity of the release movement allowed by the device is discernable higher than that allowed by the Lucas® device. Also, while the compression stroke achieves a peak in both devices, the AutoPulse® waveform exhibits an extended period without movement (the flat portion indicated as the compression hold) while the Lucas® device waveform indicates an immediate transition to upward movement, followed by a gently increasing upward velocity after the maximum point marked as item 58. The Lucas® device does not exhibit the apparent "ringing" or "hunting" at the start of the inter-compression pause, indicated by overshoot peaks 52 and 53. The upstroke overshoot peak 52 corresponds to rapid and complete release of the AutoPulse® compression belt, while the cinching overshoot peak 53 is caused by the cinching action of the belt, as it is tightened to keep the chest in a state of compression between compression cycles.

Because the manual CPR waveform is readily distinguishable from mechanical CPR waveform, and different mechanical CPR devices produce waveforms readily distinguishable from each other, a computerized control system can readily interpret the waveforms and determine how chest compressions are being performed. This may be accomplished through signal processing techniques which identify the features of the waveforms (using signal processing and feature extraction techniques similar to those used to detect features of ECG waveforms). Thus, where the patient is fitted with a compression monitor and defibrillation electrodes and an associated defibrillator with a control system operable to receive and interpret motion signals from the chest compression monitor, receive and interpret ECG signals from the electrodes to determine (through shock advisory algorithms) if electrotherapy such as defibrillating/cardioverting shock is indicated, and deliver electrotherapy to the patient through the electrodes, the control system may also be programmed to automatically detect compression waveforms and interpret the compression waveforms to distinguish manual CPR from mechanical CPR, and distinguish belt-CPR from piston-CPR, and prohibit delivery of electrotherapy (while compressions are ongoing at a resuscitative rate) when the waveform characteristics indicate that CPR chest compressions are being performed manually, or being performed by a mechanical device which has not been validated for synchronized CPR chest compressions and electrotherapy, and, in the case that the control system determines that CPR chest compressions are provided by an automated chest compression device, permit the delivery of electrotherapy according to the shock/no shock algorithms while compressions are ongoing at a resuscitative rate. (For AED systems which apply shock on demand of the CPR provider, the control system may, instead of absolutely preventing delivery of electrotherapy while manual compressions are ongoing, operate the interface to provide warnings to the CPR provider and require additional operator input prior to delivery electrotherapy while manual CPR chest compressions are ongoing.) The control system is implemented to control delivery of electrotherapy in the systems of FIGS. 1 through 5.

Compressions are considered ongoing at a resuscitative rate when one or more compression cycles are immediately followed by, or preceded by, another CPR compression performed at a resuscitative rate (which may be any rate of compressions considered effective to induce blood flow in a cardiac arrest victim, typically 60 to 120 compressions per minute), but not when the patient is not being actively compressed, such as happens during ventilation pauses, ECG analysis pauses, and other cessations of compressions or quiescent periods between sets of compressions. The electrotherapy can be delivered in synchronized fashion, at specific points in the compression cycle known to increase the efficacy of shock (typically at or near the deepest point of compression), according to the depth as determined by the chest compression monitor and control system. The control system can be programmed to apply electrotherapy, according to shock/no shock algorithms, whenever compressions are no longer ongoing at a resuscitative rate, such as during ventilation pauses, ECG analysis pauses, and other cessations of compressions or quiescent periods between sets of compressions, regardless of the source of previously detected compressions.

Determination of compression rate and its periodicity is readily accomplished through signal processing techniques (though the exact technique is not critical or essential). The control system is programmed to determine the compression rate and periodicity, and compare the measured compression rate and periodicity and variation from perfect periodicity with predetermined values. Upon determination that the compression rate conforms a predetermined compression rate (that corresponds to known chest compression devices such as the AutoPulse®), the control system may allow the AED function of delivering electrotherapy while compressions are ongoing. (Or conversely, upon determination that the compression rate deviates substantially from a predetermined rate (that corresponds to the compression rate accomplished by known chest compressions devices such as the AutoPulse®), the control system will disable the AED function of delivering electrotherapy while compressions are ongoing, specially disabling the function of delivering electrotherapy while the chest compression monitor indicates that the chest is compressed. The control system may further disable the electrotherapy function for a short period after the cessation of compressions is determined and/or disable the shock function until it receives input from the CPR provider through the interface that indicate that the CPR provider is clear of the patient (this is to ensure that a CPR provider performing manual compressions has adequate time to remove his hands from the patient).) The degree of deviation from the expected compression rate of an automated chest compression device, which would indicate that compression are accomplished manually, may be assumed to be less than about 5% compressions per minute. Thus, for AutoPulse® compressions, a detected compression rate of 76 to 84 compressions per minute may be taken as confirmation that compressions are being performed by the automated chest compression device. Chest compression rates of less than 76 or more than 84 compressions per minute would indicate that chest compressions are being performed manually. Detection of significantly higher compression rates would indicate that the AutoPulse® compression device is not in use. If other devices such as the Lucas® device are validated for synchronized shock during compressions, a similar detection scheme would apply, in which a detected compression rate between 95 and 105 compressions per minute would indicate that a Lucas® device is in use, and compression outside that range would indicate that CPR is provided manually (unless, of course, the compression rate is constant and within the range expected of the AutoPulse® device).

For discrimination between manual and automated compression based on consistency or inconsistency of the periodicity of the compressions, the control system is programmed to determine the time between compressions, using any feature of the compression waveform (the start of the downstroke, for example). This may be determined through signal processing techniques (though the exact technique is not critical or essential). Upon determination that the time between compressions is consistent and conforms to a predetermined periodicity (that corresponds to a known chest compression device such as the AutoPulse® or Lucas®), the control system may allow the AED function of delivering electrotherapy while compressions are ongoing. (Or conversely, upon determination that the periodicity deviates substantially from a predetermined periodicity (that corresponds to the periodicity accomplished by known chest compressions devices such as the AutoPulse®), the control system will disable the AED function of delivering electrotherapy while compressions are ongoing, specially disabling the function of delivering electrotherapy while the chest compression monitor indicates that the chest is compressed. The control system may further disable the shock function for a short period after the cessation of compressions is determined and/or disable the shock function until it receives input from the CPR provider through the interface that indicate that the CPR provider is clear of the patient (this is to ensure that a CPR provider performing manual compressions has adequate time to remove his hands from the patient).) The degree of deviation from the expected periodicity of an automated chest compression device, which would indicate that chest compressions are accomplished manually, may be assumed to be less than about 5%. Thus, for AutoPulse® compressions which should have a periodicity of 750 milliseconds, a series of compressions with a detected periodicity of 713 to 787 may be taken as confirmation that compressions are being performed by the automated chest compression device. Thus, for AutoPulse® compressions, a detected deviation of less than 37.5 milliseconds may be taken as confirmation that compressions are being performed by the automated chest compression device. Deviation of more than 37.5 milliseconds between successive compressions would indicate that chest compressions are being performed manually. If other devices such as the Lucas® device are validated for synchronized shock during compressions, a similar detection scheme would apply, in which a detected periodicity between 570 and 630 milliseconds would indicate that a Lucas® device is in use, and periodicity outside that range would indicate that CPR is provided manually (unless, of course, the periodicity is constant and within the range expected of the AutoPulse® device).

Determination of compression depth and its consistency is readily accomplished through signal processing techniques (the exact technique is not critical). The control system is programmed to determine the compression depth, and compare the measured compression depth and variation of compression depth from compression to compression with predetermined values. Upon determination that the compression depth consistently conforms a predetermined compression rate (that corresponds to known chest compression devices such as the AutoPulse®), the control system may allow the AED function of delivering electrotherapy while compressions are ongoing. (Or conversely, upon determination that the compression depth deviates substantially from one compression to the next (that deviates substantially from the expected of known chest compressions devices such as the AutoPulse®), the control system will disable the AED function of delivering electrotherapy while compressions are ongoing, specially disabling the function of delivering electrotherapy while the chest compression monitor indicates that the chest is compressed. The control system may further disable the shock function for a short period after the cessation of compressions is determined and/or disable the shock function until it receives input from the CPR provider through the interface that indicate that the CPR provider is clear of the patient (this is to ensure that a CPR provider performing manual compressions has adequate time to remove his hands from the patient).) The degree of deviation from the expected compression depth of an automated chest compression device, which would indicate that compression are accomplished manually, may be assumed to be ±25%, or about 0.5 inches from one compression to the next, or ±10% average from one group of compression to a following group of compressions. Thus, for AutoPulse® compressions, a detected compression depth variation of less than 0.5 inches, or preferably 0.25 inches, from one compression to the next compression, may be taken as confirmation that compressions are being performed by the automated chest compression device, especially if deviation is consistently under this threshold for a number of compressions. Chest compression depth variations of more than 0.5 inches from one compression to the next compression or a following compression would indicate that chest compressions are being performed manually (or, at least, not certainly being performed by a device).

In a similar manner, detection of the holding periods achieved by the AutoPulse® device can provide a certain indication that compressions are being performed by the AutoPulse. The AutoPulse® is programmed to compress the chest with a downstroke of about 100 milliseconds, hold the chest compressed for about 150 milliseconds (a maximum of 186 milliseconds), release the chest in a rapid upstroke (about 125 milliseconds), and hold the belt taught about the chest for about 375 milliseconds before starting the next compression downstroke 750 milliseconds after the start of the previous compression downstroke. The two holding periods can be detected with signal processing techniques (the exact technique is not critical). They are discernable as portions of the compression waveform in which the compression depth is unchanging, the velocity is zero, and the acceleration is zero. The duration of these holding periods is predetermined by the programming of the AutoPulse, but may vary depending on patient characteristics (for example, the compression hold may be shorter is it takes the device longer to compress the chest to the target compression depth). Detection of these holding periods can be used to confirm that chest compressions are being performed by an AutoPulse® device. Though the device operates perfectly consistently, the hold periods as detected by the chest compression monitor may show some minor deviation in the hold periods. However, manual compressions are characterized by very little compression hold, and very inconsistent duration of the hold between compressions. Compression holds averaging about 50 milliseconds with deviations less than about 5 or 10 milliseconds, while compression depth varies less than 5%, are indicative of AutoPulse® compressions. Thus, the control system is programmed to interpret the absence of a compression hold, or detection of a compression hold of less than 50 milliseconds, or detection of compression hold in excess of 250 milliseconds and/or deviations of greater than ±5% between successive compressions as indicative of manual compressions.

The control system can also distinguish compressions accomplished by an AutoPulse® chest compression device and a piston-based chest compression device by detecting waveform features identified in the discussion of FIGS. 10, 11, 12 and 13. The Lucas® piston-based chest compression device is configured to compress the chest with a short pause between compressions, but with little or no compression hold. The chest compression monitor waveform reflects the absence of the compression hold. The detection of a consistent hold between compressions, combined with the detection of immediate upward movement after the downstroke (that is, absence of a compression hold period between the upstroke and the downstroke) is indicative of the use of a piston-based compression device. The control system is programmed to disable the AED function of delivering electrotherapy while compressions are ongoing, specially disabling the function of delivering electrotherapy while the chest compression monitor indicates that the chest is compressed. Alternatively, when synchronized shock is validated with this chest compression technique, the control system may be programmed to permit electrotherapy during compressions, and may synchronize the delivery of shock with a point in the compression cycle most appropriate for piston-based compressions.

Also, failure to detect the compression overshoot peak 51, upstroke overshoot peak 53 or cinching overshoot peak 53 indicates that compression are not performed by the AutoPulse®. Detection of the compression overshoot peak 51 or upstroke overshoot peak 53 and/or cinching overshoot peak 53 indicates that compression are being performed by the AutoPulse® compression device. Likewise, detection of the compression hold indicates that compression are being performed by the AutoPulse® compression device, while detection of a stable and consistent inter-compression hold is indicative of automated CPR, which might be accomplished with either the AutoPulse® of the Lucas® device.

Discrimination between different modes of CPR chest compressions may be accomplished with any of the parameters discussed above, either alone or in combination. It may be beneficial to detect two or more characteristics, or the absence of characteristics, to more certainly discriminate. Using the parameters discussed above, this can be readily accomplished. For example, detection of compression overshoot peak 51 or upstroke overshoot peak 53, combined with an extended period or bounded period of minimal movement of the chest compression monitor for an extended period after the overshoot (for example, at least 100 milliseconds at the same depth during the compression hold), corresponding to the compression hold in FIG. 11), and/or not more than 400 or 500 milliseconds at the inter-compression pause, after the respective overshoots are detected, indicates that an AutoPulse® device is certainly in use. Many such combinations can be used. For example, consistent periodicity of 600 milliseconds combined with absence of a compression hold, indicates that compressions are certainly performed by a Lucas® compression device, while consistent periodicity of 750 milliseconds combined with detection of a compression hold indicates that compressions are certainly performed by an AutoPulse® compression device. In another example, compression rate of 80 or 100 compressions per minute, combined with consistent periodicity, detection of overshoot peaks, detection of a compression holds, or any other waveform characteristic will confirm that a chest compression device is in use, and confirm which of the known devices is in use. The benefits of using one parameter, or one combination of parameters, may be obtained without the use of other parameters or combination of parameters.

All of the methods for discriminating manual and automatic CPR discussed above have the advantage that they can be implemented with current compression devices, automatic external defibrillators, and compression monitors, and require no interoperability with the compression device and no modifications or additions to current devices. The necessary waveform is derived from a single motion sensor, such as the accelerometers or magnetic velocity sensors already in use, without the need for additional signal inputs. All that is needed is the sensors disposed within the chest compression monitor housing. However, additional sensors may be added to the system to provide additional signals to the control system, and the control system can be programmed to analyze these signals and incorporate them into the discrimination process. An additional accelerometer, velocity sensor or other motion sensor can be applied to the patient's chest, disposed on the electrode assembly 3, at the perimeter of the sternum electrode or the apex electrode 5, so as to be remote from the sternal bridge 6 and compression monitor 7. In use, these devices would be impacted by the compression band of the AutoPulse® compression device, and move in unison with the chest compression monitor, but would not be so impacted by manual compressions or the plunger of the Lucas® device, and movement incident to chest compressions would not be so closely tied to movement of the chest compression monitor. Also, contact sensors or pressure sensors disposed on or near the patient's chest, most conveniently on the electrode assembly, again located away from the compression point for manual and piston CPR by within the area impacted by the compression belt, would provide signals to the control system indicative of the presence or absence of a chest compression belt. Piezo-electric pressure sensors, resistive carbon ink, pressure sensitive fabric, or any other contact sensor can be used to implement this feature.

Also, a chest compression device can be modified to provide a signal to a control system through the motion sensor, without any need to provide information from the compression device to the control system through electrical or electronic communications systems. This can be done by altering the behavior of the compression device in a manner alters the compression waveform in a manner that can be detected by the motion sensor and control system. The compression waveform can be used as a signaling device, for example by consistently varying the compression rate or periodicity, or introducing chatter into the waveform.

Figure 14:
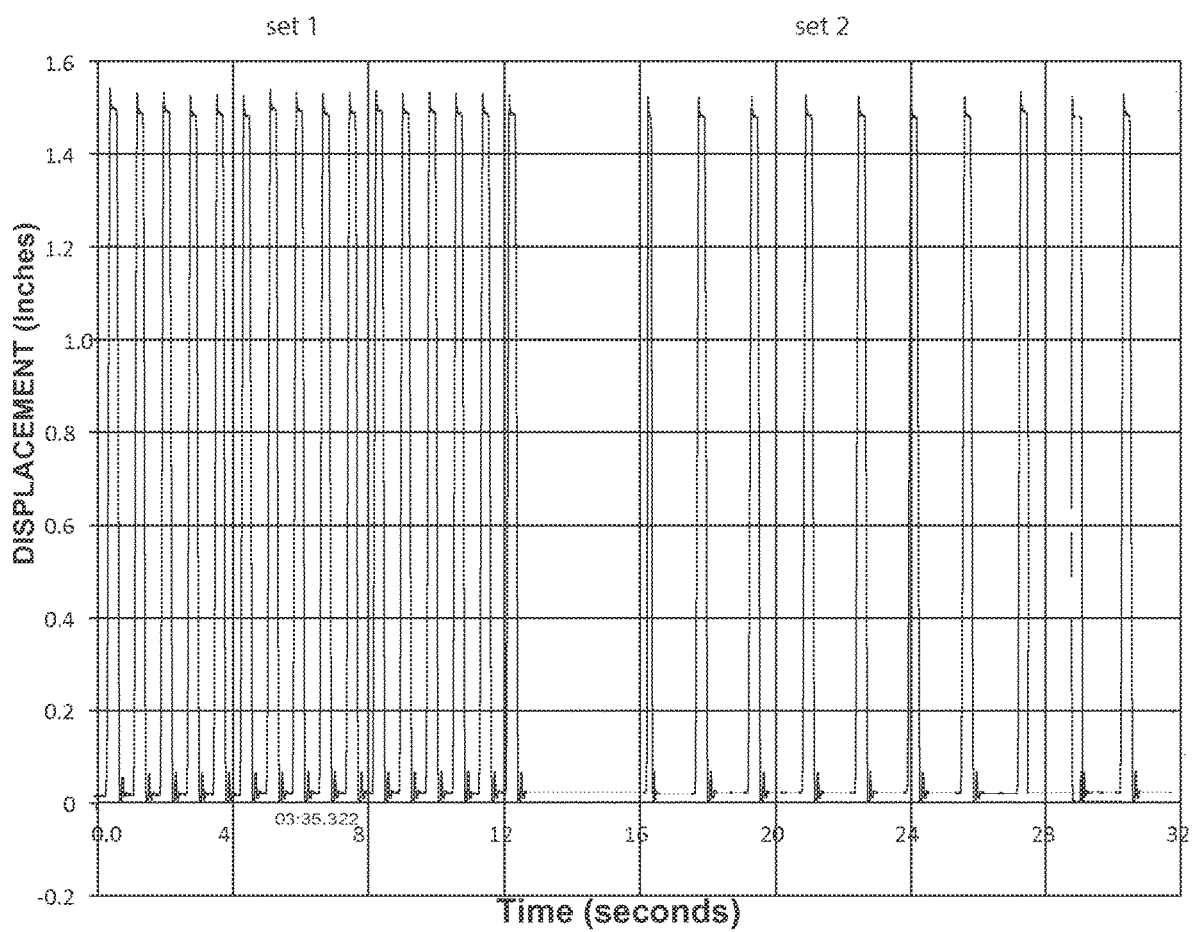
FIG. 14 illustrates sets of compression waveforms which are varied through operation of a chest compression device so as to be uniquely identifiable.

This is illustrated in FIGS. 14 and 15. FIG. 14 shows a waveform from a compression device programmed to consistently vary the compression rate, providing an occasional set of compressions at a predetermined distinctly different compression rate. Two compression sets are depicted in FIG. 14. Set 1 is performed at 80 compressions per minute, while set two is performed at 60 compressions per minute. The control system can be programmed to detect the predetermined compression rate for a set of compressions, amongst other sets of compressions, and thereby determine that a specific chest compression device is in use. FIG. 15 shows a waveform from a compression device programmed to provide a stutter in the compression waveform, for example an easily detectable peak or inflection point at a point in the compression cycle. For example, during downstroke or the upstroke, preferable toward the end of the upstroke, the system can momentarily brake the belt (using a brake as described previous patents pertaining to the AutoPulse® compression device, such as Mollenauer, Method Of Performing CPR With A Modular CPR Assist Device Using A Brake To Momentarily Hold A Belt At A Threshold Of Tightness, U.S. Pat. No. 8,062,239 (Nov. 22, 2011)) or slowing or speeding up the motor, to insert a notch or inflection point in the waveform. These notches are marked as item 59 in FIG. 15. The control system can be programmed to detect the notch in the waveform, and thereby determine that a specific chest compression device is in use.

FIGS. 10 through 15 illustrate the discrimination method using compression depth waveforms. Similar analysis may be accomplished using the corresponding acceleration waveforms and velocity waveforms, so that any compression waveform may be analyzed, as described above, to detect unique and distinguishing characteristics of the waveform derived from manual CPR chest compressions and automatic compression devices, and discriminate waveforms based on distinguishing or peculiar features of the waveforms and thus determine the source of chest compressions. Thus, where an accelerometer is used for the motion sensor, the acceleration waveform need not be integrated to obtain a chest compression depth waveform in order to accomplish the discriminating method.

All of the discriminating methods described above are preferably accomplished through a control system, which may be located within the defibrillator control system, within the chest compression monitor, or may be provided as a separate control system. As described above, the system includes a chest compression monitor comprising a motion sensor operable to provide motion signals indicative of motion of cardiac arrest victim's chest during CPR chest compressions, defibrillation electrodes and an associated defibrillator, and an associated control system operable to receive and interpret ECG signals from the electrodes to determine if electrotherapy is indicated (according to shock advisory algorithms), and deliver electrotherapy to the electrodes and receive and interpret motion signals from the chest compression monitor to determine a compression waveform representative of the chest compressions experienced by the cardiac arrest victim and operable to interpret compression waveforms from the motion sensor to determine the source of chest compressions based on one or more compression waveform characteristics, and control delivery of electrotherapy based on the determined source of chest compressions.

The system thus implements a corresponding method of controlling a defibrillator to resuscitate a cardiac arrest victim. The method includes the steps of acquiring the motion signals from a motion sensor operable to generate motion signals corresponding to motion of the chest of the cardiac arrest victim, generating a compression waveform corresponding to motion of the chest of the cardiac arrest victim. After generation of the waveforms, the method includes the steps of operating the control system associated with the defibrillator to analyze the compression waveform to determine whether chest compressions are performed manually or by an automated chest compression device, and then operating the control system to control delivery of electrotherapy based on the determined source of chest compressions.

The control system may be programmed upon manufacture, but existing defibrillators and AED's may updated through distribution of software program in a non-transitory computer readable medium storing the program, which, when executed by a computer or the control system, makes the computer and/or the control system communicate with and/or control the various components of the system to accomplish the methods, or any steps of the methods, or any combination of the various methods, described above. These steps include making the control system generate a compression waveform corresponding to acceleration, velocity or depth of the patient's chest wall, and analyze the waveform to detect waveform features indicative of a source of CPR chest compressions, and thereby determine the source of CPR chest compressions, making the control system operate the defibrillator to apply electrotherapy to the patient while compression are ongoing if, and only if, the control system determines that the source of CPR chest compressions is an automated chest compression device, and making the control system operate the defibrillator to apply electrotherapy to the patient while compression are ongoing if, and only if, the control system determines that the source of CPR chest compressions is an automated chest compression device.

In the description above, the term periodicity has been used to refer to a characteristic of the compression waveform. Periodicity refers to the regularity of the time between compressions, which may be measured by the time between detection of any portion of one waveform and the detection of that same portion of next or previous waveform. It may refer to the time between the detected start of successive compression strokes, successive peak compression depth, successive compression stroke overshoot peaks, or other portion of the waveform. Thus, a series of compressions having exactly the same period has a high (perfect) periodicity, while a series of compressions having highly variable periods will have low periodicity. The term compression rate refers to the average rate of compressions over a time period. Compressions may be performed at a compression rate expressed in compressions per minute, for several sets separated by ventilation pauses, such that the average compression rate, over a span of several sets, is lower than compression rate. If no pauses are provided by an automated CPR compression device, the average compression rate and the compression rate should be the same. Also, compressions might be performed at a steady compression rate, but have low periodicity, as for example, a manual provider might provide compressions at a compression rate that matches a known chest compression device, but it is highly unlikely that the periodicity of those manual compressions will match the invariable periodicity of an automatic device.

The term "automated chest compression device" refers to chest compression devices that are controlled by computerized control systems, electro-mechanical systems, or the like, such that the compression rate, periodicity, compression depth and other compression waveform characteristics are predetermined by the programming or design of the device, and are not subject to variability due to the physical actions of a CPR provider (other than providing input to the control system or adjusting set points for an electromechanical system). Manual CPR chest compressions refer to classic two-hand CPR as illustrated in the ACLS guidelines, as well as mechanically assisted CPR using devices that, though mechanical in nature, depend on the physical activity of the CPR provider to control compression waveform characteristics (such as the hand-powered device shown in Lach, et al., Resuscitation Method and Apparatus, U.S. Pat. No. 4,770,164 (Sep. 13, 1988)). The inventions have been described in relation to two commercially available automated chest compression devices, but may be applied to any automated chest compression devices.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A system for use during administration of cardiopulmonary resuscitation (CPR) chest compressions on a victim from a source of the chest compressions, the system comprising:
   a chest compression monitor comprising a motion sensor configured to generate signals indicative of motion of the chest of the victim during the chest compressions; and
   a control system communicatively coupled to the chest compression monitor, the control system configured to:
      receive the generated signals indicative of the motion of the chest of the victim during the chest compressions;
      detect one or more compression waveform features representative of the chest compressions based on the received signals;
      compare the detected one or more compression waveform features to a pre-determined criterion that distinguishes between a manual source of the chest compressions and a piston-based chest compression device source of the chest compressions;
      determine whether the source of the chest compressions is the manual source or the piston-based chest compression device source based on the comparison with the pre-determined criterion; and
      generate an output that is based on whether the source of the chest compressions is determined to be the manual source or the piston-based chest compression device source.

2. The system of claim 1 wherein the control system is configured to detect the one or more compression waveform features in a chest wall displacement waveform.

3. The system of claim 2 wherein the one or more compression waveform features comprises a variation of a displacement over a plurality of chest compression cycles and the pre-determined criterion is a degree of the variation of the displacement over the plurality of chest compression cycles.

4. The system of claim 3 wherein, if the degree of the variation of the displacement between compression cycles is a variation within ±25% of a target displacement, then the source of the chest compressions is the piston-based chest compression device source, else the source of the chest compressions is the manual source.

5. The system of claim 2 wherein the one or more compression waveform features comprises a variation of a compression rate over a plurality of chest compression cycles and the pre-determined criterion is a degree of the variation of the compression rate over the plurality of chest compression cycles from an average compression rate over the plurality of chest compression cycles.

6. The system of claim 5 wherein, if the degree of the variation of the compression rate is a variation within ±5% of the average compression rate across the plurality of chest compression cycles, then the source of the chest compressions is the piston-based chest compression device source, else the source of the chest compressions is the manual source.

7. The system of claim 2 wherein the control system is configured to detect a curvature of a transition in each chest compression cycle between a downstroke and an upstroke as represented by the chest wall displacement waveform.

8. The system of claim 2 wherein the control system is configured to detect an inter-compression hold between each chest compression cycle based on a shape of the chest wall displacement waveform between each chest compression cycle represented in the chest wall displacement waveform.

9. The system of claim 8 wherein the pre-determined criterion is a consistency over a plurality of chest compression cycles of a duration of the inter-compression hold.

10. The system of claim 1 wherein the control system is configured to detect one or more of a peak velocity of a compression downstroke, a peak acceleration of the compression downstroke, a peak velocity of a compression upstroke, and a peak acceleration of the compression upstroke.

11. The system of claim 1 wherein the control system is configured to detect one or more of a compression overshoot peak, an upstroke overshoot peak, and a cinching overshoot peak.

12. The system of claim 1 wherein the signals indicative of motion of the chest of the victim during the chest compressions comprise one or more of acceleration signals, velocity signals, and distance signals.

13. The system of claim 1 further comprising:
an electrotherapy device; and
electrotherapy electrodes,
wherein the output is configured to control delivery of electrotherapy by the electrotherapy device.

14. The system of claim 13 wherein the output prohibits the delivery of the electrotherapy by the electrotherapy device when the source of the chest compressions is determined to be the manual source, but allows the delivery of the electrotherapy by the electrotherapy device when the source of the chest compressions is determined to be the piston-based chest compression device source.

15. The system of claim 13 wherein the electrotherapy device is a defibrillator.

16. The system of claim 13 wherein the control system is further configured to:
receive electrocardiogram (ECG) signals from the electrotherapy electrodes; and
determine if the electrotherapy is indicated based on the ECG signals.

17. The system of claim 13 wherein the electrotherapy is one or more of defibrillation, cardioversion, and electrical nerve stimulation.

18. The system of claim 1 further comprising a piston-based chest compression device wherein the output is configured to control chest compressions provided by the piston-based chest compression device.

19. The system of claim 1 wherein the output provides feedback for a rescuer wherein the feedback is communicable by an input/output device.

20. The system of claim 19 wherein the input/output device comprises one or more of an annunciator and a display.

21. The system of claim 19 wherein the feedback for the rescuer comprises one or more of audio feedback and visual feedback.

22. The system of claim 19 wherein the feedback for the rescuer comprises one or more of compression rate prompts, compression depth prompts, and compression release prompts.

23. The system of claim 22 wherein the signals indicative of the motion of the chest of the victim comprise signals indicative of a current compression rate and the compression rate prompts comprise prompts to compress at a faster compression rate than the current compression rate or at a slower compression rate than the current compression rate.

24. The system of claim 22 wherein the signals indicative of the motion of the chest of the victim comprise signals indicative of a current compression depth and the compression depth prompts comprise prompts to compress more deeply than the current compression depth.

25. The system of claim 22 wherein the compression release prompts comprise prompts after each compression to quickly and completely release the chest of the victim.

* * * * *